(12) United States Patent
Walkinshaw et al.

(10) Patent No.: US 7,223,795 B2
(45) Date of Patent: May 29, 2007

(54) MODIFIED PEPTIDE DERIVATIVES AND METHODS OF USE THEREOF

(75) Inventors: Malcolm Douglas Walkinshaw, Edinburgh (GB); Paul Taylor, Edinburgh (GB); Nicholas John Turner, Edinburgh (GB); Sabine Lahja Flitsch, Edinburgh (GB)

(73) Assignee: Cyclacel Limited, London (GB)

( * ) Notice: Subject to any disclaimer, the term of this patent is extended or adjusted under 35 U.S.C. 154(b) by 181 days.

(21) Appl. No.: 10/461,208

(22) Filed: Jun. 12, 2003

(65) Prior Publication Data

US 2004/0077829 A1    Apr. 22, 2004

Related U.S. Application Data

(63) Continuation of application No. PCT/GB01/05540, filed on Dec. 31, 2001.

(30) Foreign Application Priority Data

Dec. 13, 2000 (GB) .................................. 0030378.4

(51) Int. Cl.
*A61K 31/24* (2006.01)
*C07C 269/04* (2006.01)
*C07C 271/22* (2006.01)
*G01N 33/00* (2006.01)

(52) U.S. Cl. .................... 514/533; 560/158; 436/86

(58) Field of Classification Search ............... 560/158; 436/86; 514/533
See application file for complete search history.

(56) References Cited

FOREIGN PATENT DOCUMENTS

| JP | 52-034530 | 9/1977 |
|---|---|---|
| WO | WO 96/14339 A1 | 5/1996 |
| WO | WO 96/35715 A2 | 11/1996 |
| WO | WO 97/11174 A1 | 3/1997 |
| WO | WO 97/42222 A1 | 11/1997 |
| WO | WO 98/25950 A1 | 6/1998 |
| WO | WO 99/64574 A1 | 12/1999 |

OTHER PUBLICATIONS

Braaten, et al. Cyclophilin A regulates HIV-1 infectivity, as demonstrated by gene targeting in human T cells. EMBO J. Mar. 15, 2001;20(6):1300-9.
Christner, et al. Synthesis and cytotoxic evaluation of cycloheximide derivatives as potential inhibitors of FKBP12 with neuroregenerative properties. J Med Chem. Sep. 9, 1999;42(18):3615-22.
Gallo, et al. Specific interaction between cyclophilin and cyclic peptides. Biopolymers. Sep. 1995;36(3):273-81.
Kallen, et al. The X-ray structure of a tetrapeptide bound to the active site of human cyclophilin A. FEBS Lett. Apr. 6, 1992;300(3):286-90.
Taylor, et al. Structures of cyclophilin-ligand complexes. Prog Biophys Mol Biol. 1997;67(2-3):155-81.
Zhao, et al. Mechanistic implication of crystal structures of the cyclophilin-dipeptide complexes. Biochemistry. Jun. 11, 1996;35(23):7362-8.

*Primary Examiner*—Taofiq Solola
(74) *Attorney, Agent, or Firm*—Lahive & Cockfield, LLP; Cynthia L. Kanik; Cynthia M. Soroos, Esq.

(57) ABSTRACT

The present invention relates to a compound of formula I

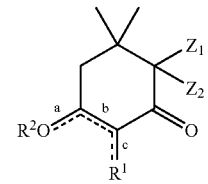

wherein
(i) when a and c are double bonds, $R^2$ is absent, b is a single bond,
$R^1$ is

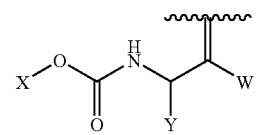

or
(ii) when a and c are single bonds, b is a double bond, and $R^1$ is H,
$R^2$ is

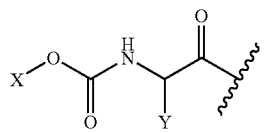

wherein the substituents are as defined in the specification.

19 Claims, 2 Drawing Sheets

MODIFIED PEPTIDE DERIVATIVES AND METHODS OF USE THEREOF

RELATED APPLICATIONS

This application is a continuation application of serial number PCT/GB01/05540 filed on Dec. 13, 2001; which claims priority to Great Britain application number 0030378.4, filed Dec. 13, 2000. The contents of the aforementioned applications are hereby incorporated by reference.

BACKGROUND OF THE INVENTION

The present invention relates to modified peptide derivatives.

Many therapeutic agents operate by interacting with enzymes or receptors to modify their activity in a therapeutically beneficial manner. In the search for novel therapeutic agents it is thus sensible to concentrate on molecules which possess some degree of structural and conformational analogy with the natural substrate or ligand. Very often the identity of the natural substrate or ligand is unknown, but in many cases it can be inferred that a polypeptide is involved. It is therefore desirable to focus on compounds based on naturally occurring peptide structures, which can be screened for efficacy in interacting with the enzymes and/or receptors of interest.

It is known that the interaction of proteins controls key aspects of cellular function. For example protein-protein interactions control the signalling process causing a cell to divide, the malfunctioning of which may lead to cancer and other proliferative diseases. It has previously been demonstrated that an isolated peptide having the same sequence as the active portion of a natural protein may be used to bind with the natural protein-binding partner, and to elicit the same biological response. Processes of this type are described, for example, in WO97/11174, WO96/14339, WO96/35715 and WO97/42222.

Previous studies by the applicant have revealed that a range of non-peptide molecules may be used to mimic the structure of specific peptides within the natural polypeptide binding partners of various proteins which naturally bind protein ligands, and which may be used to interact with those proteins. This work is further described in WO 99/64574.

Of particular interest to the applicant are novel cyclophilin binding ligands. Cyclophilins are ubiquitous proteins highly conserved during evolution. They are found in bacteria, fungi, plants and vertebrates, and are widely expressed in many tissues. At least eight different forms of human cyclophilins have been identified, ranging from 18 kDa to 150 kDa in molecular mass [Göthel et al, Cell Mol. Life Sci 1999, 55, 433–436].

Cyclophilin is the major intracellular receptor for the immunosuppressive drug cyclosporin A [Handschumacher et al, Science 1984, 226,544–547]. In particular, cyclosporin A acts as an inhibitor of T-cell activation and can prevent graft rejection in organ and bone marrow transplantation [Borel, Pharmac. Review, 1969, 41, 259–371]. Cyclophilin is believed to be responsible for mediating this immunosuppressive response.

In addition, cyclophilin is also known to catalyse the interconversion of the cis and trans isomers of the peptidyl-prolyl amide bonds of peptide and protein substrates [Takahashi et al, Nature 1989, 337, 473–375; Fischer et al, Nature 1989, 227, 476–478]. Indeed, cyclophilin has been reported to accelerate the isomerisation of peptidyl-prolyl bonds in protein folding [Fisher et al, Biochemistry 1990, 29, 2205–2212]. Several mechanisms have been proposed including catalysis by (i) formation of a tetrahedral intermediate, (ii) distortion, (iii) protonation of the amide nitrogen, (iv) desolvation, or (v) a solvent assisted mechanism.

In order to elucidate the binding site for cyclosporin A, X-ray crystallographic studies have been carried out on a number of cyclosporin A-cyclophilin complexes. For example, Kallen et al [Nature 1991, 353, 276–279] disclose the X-ray crystal structure of human recombinant cyclophilin complexed with a tetrapeptide and identify the specific binding site for cyclosporin A by means of NMR spectroscopy. It was further revealed that the prolyl isomerase substrate binding site is coincident with the cyclosporin A binding site. Such results help provide a structural basis for rationalising the immunosuppressive function of the cyclosporin A-cyclophilin system and may also be important in the rational design of improved immunosuppressive drugs.

Studies by Zhao et al [Biochemistry 1996, 35, 7362–7368] disclose high resolution structures of cyclophilin A complexed with dipeptides of Ser-Pro, His-Pro and Gly-Pro. A comparison of these cyclophilin complexes reveals that the dipeptide structures have the same molecular conformation and bind in a similar manner. Moreover, the side chains of the N-terminal amino acids of the dipeptides do not strongly interact with cyclophilin, implying a minor contribution to any cis-trans isomerisation activity, thus accounting for the broad catalytic specificity of the enzyme.

WO98/25950 (Guildford Pharmaceuticals Inc.) discloses that small proline-containing tetra- or pentapeptides have a high affinity for cyclophilin-type immunophilins. Similarly, X-rays studies by Kallen and Walkinshaw [FEBS Letters, 1992, vol. 300, no. 3, 286–290] disclose the structure of a tetrapeptide bound to the active site of cyclophilin A, whereas Gallo et al [Biopolymers 1995, 36, 273–8] disclose binding experiments of cyclolinopeptide A [cyclo(-Pro$^1$-Pro$^2$-Phe$^3$-Ph$^4$-Leu$^5$-Ile$^6$-Ile$^7$-Leu$^8$-Val$^9$)] with cyclophilin A.

In view of the properties described above, cyclophilin binding ligands are likely to be medically useful as inhibitory drugs. Indeed, the recent discovery that inhibition of cyclophilin prevents its incorporation into the HIV protein coat suggests that families of inhibitors unrelated to the immunosuppressant cyclosporins may provide potential anti-HIV drugs. Moreover, the development of species-specific cyclophilin inhibitors may also provide a route to novel anti-parasitic drugs.

The link between cyclophilin A and HIV has been the subject of a recent publication by Braaten D. and Luban J. [EMBO J Mar. 15, 2001;20(6):1300–9] which confirms the role of cyclophilin A in the regulation of the infectivity of HIV-1 virions.

Cyclophilin has also been implicated in certain types of cancer. For example, cyclophilin 40 is known to be overexpressed in breast tumours, compared to normal breast tissue [Breast Cancer Research and Treatment, 58, 267–280]. Estradiol treatment over a period of 24 hours has been shown to lead to a 5-fold increase in the expression of cyclophilin 40 mRNA in MCF-7 breast cancer cells [Biochemical and Biophysical Research Communications, 2001, 284, 219–225]. Further studies have revealed that allelic loss is detected in 30% of breast carcinomas from patients heterozygous for the cyclophilin 40 marker, suggesting that deletions of the cyclophilin 40 gene might be a late event in breast tumour progression [Journal Of Cancer Research And Clinical Oncology, 2001, 127, 109–115]. Cyclophilin 40 is also believed to play a role in liver cancer [Carcinogenesis, 2000, 21, 647–652].

Cyclophilin B has also been implicated in cancer. In this regard, Gomi et al have reported that the cyclophilin B gene encodes antigenic epitopes recognised by HLA-A24-restricted and tumour specific CTLs [Gomi S, Nakao M, Niiya F, Imamura Y, Kawano K, Nishizaka S, Hayashi A, Sobao Y, Oizumi K, Itoh K., J Immunol Nov. 1, 1999;163(9):4994–5004]. Tamura et al have identified a number of cyclophilin B-derived peptides capable of inducing histocompatability leukocyte antigen-A2-restricted and tumour-specific cytotoxic T lymphocytes [Tamura M, Nishizaka S, Maeda Y, Ito M, Harashima N, Harada M, Shichijo S, Itoh K., Jpn J Cancer Res, July 2001;92(7):762–7]. The present invention seeks to provide novel compounds which are capable of either binding to or inhibiting cyclophilin.

DETAILED DESCRIPTION

In a first aspect, the invention provides a compound of formula I

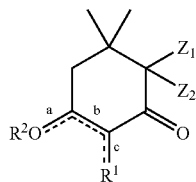

wherein
(i) when a and c are double bonds, $R^2$ is absent, b is a single bond,
$R^1$ is

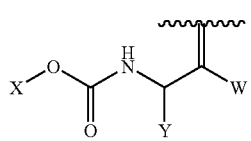

or
(ii) when a and c are single bonds, b is a double bond, and $R^1$ is H,
$R^2$ is

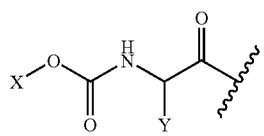

wherein X is straight or branched chain $C_{1-6}$ alkyl, —$(CH_2)_n$Ar, $C_{1-6}$ cycloalkyl, or —$(CH_2)_n$R", where R" is a cyclic hydrocarbyl group;
Y is a natural or unnatural amino acid side chain;
W is OH or $NHR^3$, wherein $R^3$ is —$CH(Y')CO_2X'$, where X' and Y' are defined as for X and Y respectively, and may be the same or different to X and Y respectively; and $Z_1$ and $Z_2$ are each independently H, straight or branched chain $C_{1-6}$ alkyl, straight or branched chain $C_{1-6}$ alkenyl, —$(CH_2)_n$Ar, —$(CH_2)_n$—$CO_2R'$, —$(CH_2)_p$—CH=CH—$(CH_2)_q$Ar where p and q are each independently 0 to 5, R' is $C_{1-6}$ alkyl;
and each n may be the same or different and is from 1 to 5.

In a preferred embodiment, the compound is of formula Ia

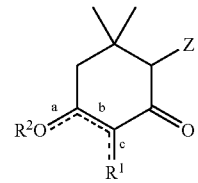

wherein
(i) when a and c are double bonds, $R^2$ is absent, b is a single bond,
$R^1$ is

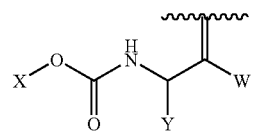

or
(ii) when a and c are single bonds, b is a double bond, and $R^1$ is H,
$R^2$ is

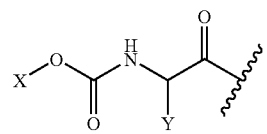

wherein X is straight or branched chain $C_{1-6}$ alkyl, —$(CH_2)_n$Ar, $C_{1-6}$ cycloalkyl, or —$(CH_2)_n$R", where R" is a cyclic hydrocarbyl group;
Y is a natural or unnatural amino acid side chain;
W is OH or $NHR^3$, wherein $R^3$ is —$CH(Y')CO_2X'$, where X' and Y' are defined as for X and Y respectively, and may be the same or different to X and Y respectively; and
Z is H, straight or branched chain $C_{1-6}$ alkyl, straight or branched chain $C_{1-6}$ alkenyl, —$(CH_2)_n$Ar, —$(CH_2)_n$—$CO_2R'$, —$(CH_2)_p$—CH=CH—$(CH_2)_q$Ar where p and q are each independently 0 to 5, R' is $C_{1-6}$ alkyl;
and each n may be the same or different and is from 1 to 5.

As used herein, the term "alkyl" refers to a $C_{1-6}$ saturated carbon-containing chain which may be straight or branched, and substituted (mono- or poly-) or unsubstituted.

As used herein, the term "alkenyl" refers to a $C_{2-6}$ unsaturated carbon-containing chain which may be branched or unbranched, and substituted (mono- or poly-) or unsubstituted.

As used herein, the term "cyclic hydrocarbyl group" refers to a $C_{4-10}$ mono- or polycyclic group, which comprises hydrogen and carbon and which may optionally comprise one or more other suitable substituents. Said mono- or polycyclic group may be saturated or unsaturated, aromatic or non-aromatic.

As used herein, the term "Ar" (aryl) refers to a $C_{6-10}$ aromatic group, substituted (mono- or poly-) or unsubstituted.

As used herein, the term "cycloalkyl" refers to a cyclic alkyl group which may be substituted (mono- or poly-) or unsubstituted.

Where X, X' or Z are substituted, suitable substituents include those which do not have any significant adverse effect on the binding of the compound to cyclophilin. Examples of such substituents may include halo-, alkoxy-, nitro-, an alkyl group, or a cyclic group. The X, X' or Z group may further comprise one or more heteroatoms. Suitable heteroatoms will be apparent to those skilled in the art and include, for instance, sulphur, nitrogen, oxygen and phosphorus.

In the structure of formula I, the —NH—CH(Y)—CO— moiety of $R^2$ and the —NH—CH(Y)—C(=C)—W moiety of $R^1$ mimic the structure of an amino acid of formula $NH_2CH(Y)CO_2H$. As used herein, the term "natural or unnatural amino acid side chain" therefore refers to the substituent corresponding to Y in any known natural or unnatural amino acid.

For example, to mimic natural amino acids, Y may be chosen as follows:

| Y | amino acid |
|---|---|
| H | glycine |
| Me | alanine |
| $CH(Me)_2$ | valine |
| $CH_2CH(Me)_2$ | leucine |
| $CH(Me)Et$ | isoleucine |
| $CH_2Ph$ | phenylalanine |
| $CH_2C_6H_4OH$ | tyrosine |
| $CH_2C_8NH_6$ | tryptophan |
| $CH_2SH$ | cysteine |
| $CH_2CH_2SMe$ | methionine |
| $CH_2OH$ | serine |
| $CH(OH)Me$ | threonine |
| $(CH_2)_4NH_3^+$ | lysine |
| $(CH_2)_3NH(C=NH_2^+)NH_2$ | arginine |
| $CH_2C_3N_2H_4^+$ | histidine |
| $CH_2CO_2^-$ | aspartate |
| $CH_2CH_2CO_2^-$ | glutamate |
| $CH_2CONH_2$ | asparagine |
| $CH_2CH_2CONH_2$ | glutamine |

Other Y substituents may also be chosen in order to produce a range of different amino acid mimicking molecules. For example, Y may be an unnatural amino acid side chain.

The term "unnatural amino acid" refers to a derivative of an amino acid and may for example include alpha and alpha-disubstituted amino acids, N-alkyl amino acids, lactic acid, halide derivatives of natural amino acids such as trifluorotyrosine, p-Cl-phenylalanine, p-Br-phenylalanine, p-I-phenylalanine, L-allyl-glycine, β-alanine, L-α-amino butyric acid, L-γ-amino butyric acid, L-α-amino isobutyric acid, L-ε-amino caproic acid, 7-amino heptanoic acid, L-methionine sulfone, L-norleucine, L-norvaline, p-nitro-L-phenylalanine, L-hydroxyproline, L-thioproline, methyl derivatives of phenylalanine (Phe) such as 4-methyl-Phe, pentamethyl-Phe, L-Phe (4-amino), L-Tyr (methyl), L-Phe (4-isopropyl), L-Tic (1,2,3,4-tetrahydroisoquinoline-3-carboxyl acid), L-diaminopropionic acid and L-Phe (4-benzyl).

In one preferred embodiment of the invention, X and X' are each independently selected from from methyl, t-butyl, 2-methylpropyl, ethyl, benzyl and

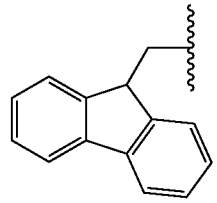

more preferably benzyl or t-butyl.

In one particularly preferred embodiment of the invention, X and X' are different.

In another preferred embodiment of the invention, Y and Y' are each independently selected from methyl, benzyl, iso-propyl and 2-methylpropyl, and are more preferably selected from iso-propyl and benzyl.

In one particularly preferred embodiment of the invention, Y and Y' are different.

In yet another preferred embodiment of the invention, Z is selected from H, methyl, benzyl, allyl, —$CH_2CO_2Me$ and —$CH_2$—CH=CH-Ph, and is more preferably H or methyl.

In one preferred embodiment, the compound of the invention is a racemate. As used herein, the term "racemate" refers to a mixture of equal quantities of the (+) or (R)- and (−) or (S)-enantiomers of an optically active compound. Such a mixture exhibits no optical activity, i.e. it does not rotate the plane of polarized light. The skilled person will appreciate that compounds of the invention containing more than one chiral centre may exist as two different stereoisomers, each of which may exist in two enantiomeric forms. Preferably, the stereochemistry of the Y substituent (and the Y' substituent, where present) of the compounds of the invention is such that the chiral centre to which it is attached is in the (S)-form.

In one embodiment, the invention provides a compound of formula II

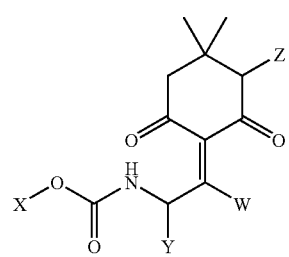

II wherein W, X, Y and Z are as defined hereinbefore.

Preferably, Z is H, Y is isopropyl, and W is OH or $NHR^3$, wherein $R^3$ is as defined above.

Even more preferably, W is OH or $NHCH(CH_2Ph)CO_2Me$.

Preferably, the compound of formula II is selected from the following:

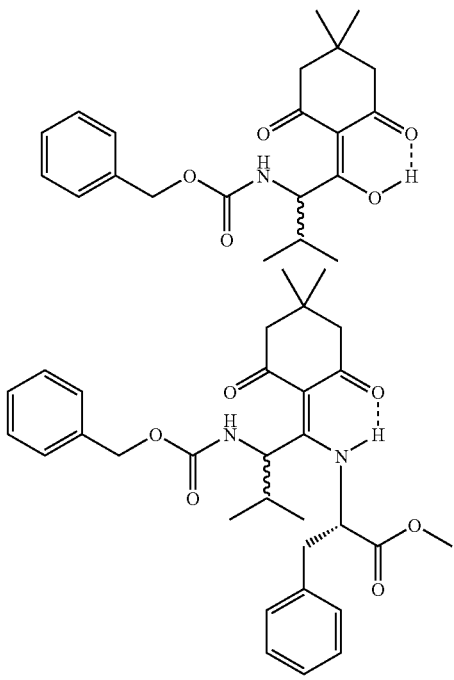

In another preferred embodiment, the invention provides a compound of formula III

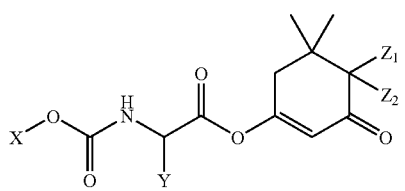

III wherein X, Y and $Z_1$ and $Z_2$ are as defined hereinbefore.

In a particularly preferred embodiment, $Z_1$ and $Z_2$ are each independently selected from H, a straight or branched $C_{1-6}$ alkyl group, or $CH_2Ph$;

Y is isopropyl, 2-methylpropyl or $CH_2Ph$;

X is $CH_2Ph$ or a straight or branched $C_{1-6}$ alkyl group.

Even more preferably, X is $^tBu$ or $CH_2Ph$.

In a particularly preferred embodiment, the invention provides a compound of formula IIIa

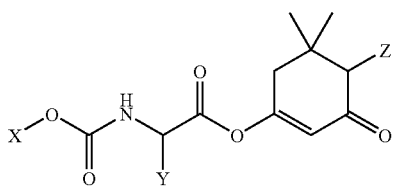

IIIa wherein X, Y and Z are as defined hereinbefore.

In a particularly preferred embodiment,

Z is H, a straight or branched $C_{1-6}$ alkyl group, or $CH_2Ph$;

Y is isopropyl, 2-methylpropyl or $CH_2Ph$;

X is $CH_2Ph$ or a straight or branched $C_{1-6}$ alkyl group.

Even more preferably, X is $^tBu$ or $CH_2Ph$.

Even more preferably, the compound of formula III is selected from the following:

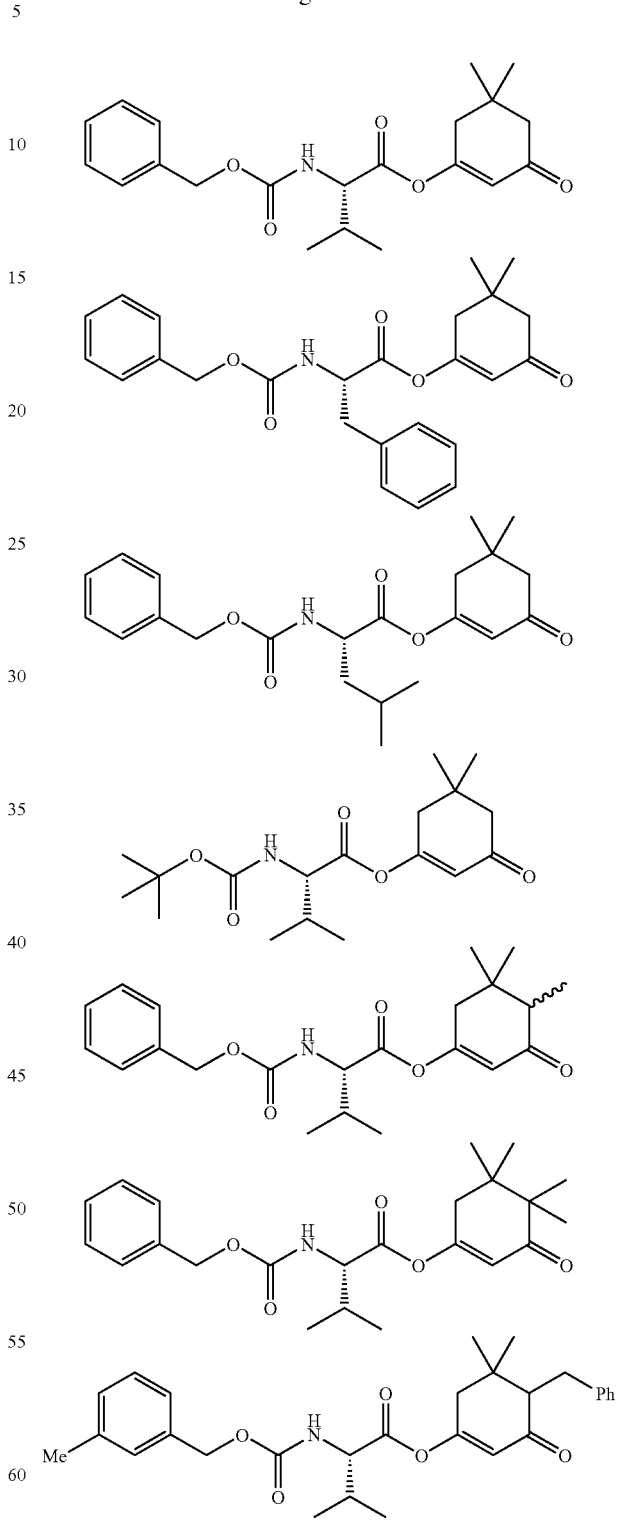

A second aspect of the invention relates to a complex comprising cyclophilin and a compound as described hereinbefore. Preferably, the cyclophilin of the complex is cyclophilin A, cyclophilin D or cyclophilin 40.

The binding interactions between a compound of formula III (EM 2/34) and cyclophilin were ascertained from inspection of the X-ray structure of the complex and are shown in schematic form below.

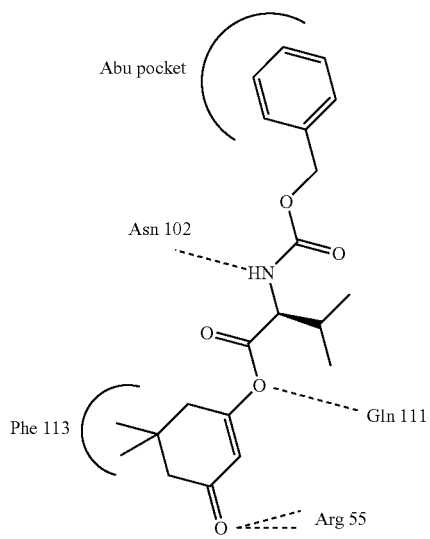

Preferably, a compound of formula III interacts with one or more of the following amino acid residues of cyclophilin: Phe 113, Arg 55, Gln 111 and Asn 102.

Binding studies have revealed that the binding constant ($K_d$) of compound EM 2/34 to cyclophilin is in the region of 1 µM. By way of comparison, $K_d$ for Cyclosporin A is 30 nM, whereas $K_d$ for dimedone is 22 mM.

Where the compound of the invention is in the form of a mixture of isomers, it is possible that one isomer may bind to cyclophilin preferentially over the other. In other words, each isomer may exhibit a different binding affinity to cyclophilin. To some extent, such differences in binding affinity may effectively allow the protein to partially or fully resolve a mixture of isomers. High resolution crystallographic studies may enable the skilled person to determine which of the isomers is the preferred ligand.

A third aspect of the invention relates to a pharmaceutical composition comprising a compound of the invention as described hereinbefore together with a pharmaceutically acceptable diluent, excipient or carrier.

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

A fourth aspect of the invention relates to a process for preparing a compound of formula III,

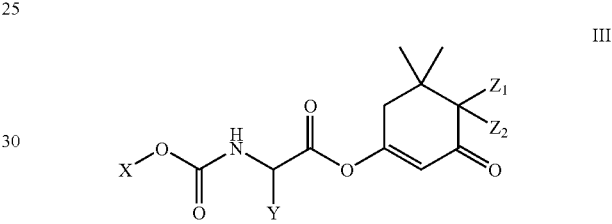

said process comprising the steps of
(i) reacting a compound of formula V with a compound of formula VI to form a compound of formula VII;

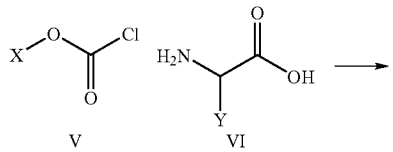

(ii) converting said compound of formula VII to a compound of formula VIII;

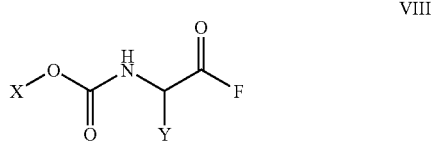

(iii) reacting said compound of formula VIII with a compound of formula IV

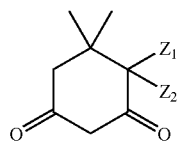

IV

In a preferred embodiment, the compound of formula VII is converted to a compound of formula VIII by treating with (CFN)$_3$/pyridine.

In a further preferred embodiment, step (iii) comprises reacting a compound of formula VIII with a compound of formula IV in the presence of N,N'-diisopropylethylamine.

As mentioned hereinbefore, preferably the stereochemistry of the Y substituent (and the Y' substituent, where present) of the compounds of the invention is such that the chiral centre to which it is attached is in the (S)-form.

The compounds of the present invention may be prepared by a more general route that is suitable for parallel library synthesis in array format. This is illustrated further in scheme 1, shown below.

As used herein the phrase "preparation of a medicament" includes the use of a compound of the invention directly as the medicament in addition to its use in a screening programme for the identification of further agents or in any stage of the manufacture of such a medicament.

Such a screening programme may for example include an assay for determining the binding to the binding site of cyclophilin and determining whether a candidate substance is capable of mimicking the activity of a compound of formula I.

Thus, in a further embodiment, the invention relates to the use of a compound of formula I or a pharmaceutically acceptable salt, crystal form, complex, or hydrate thereof, in an assay for determining binding to the PPIase binding site of cyclophilin, and optionally in the identification of candidate compounds that act in a similar manner.

In one preferred embodiment, the invention relates to an assay that is capable of identifying candidate compounds that influence the PPIase activity of cyclophilin.

In a particularly preferred embodiment of the invention, the assay is a competitive binding assay.

In one particularly preferred embodiment, the competitive binding assay comprises contacting a compound of the invention with cyclophilin in the presence of a known

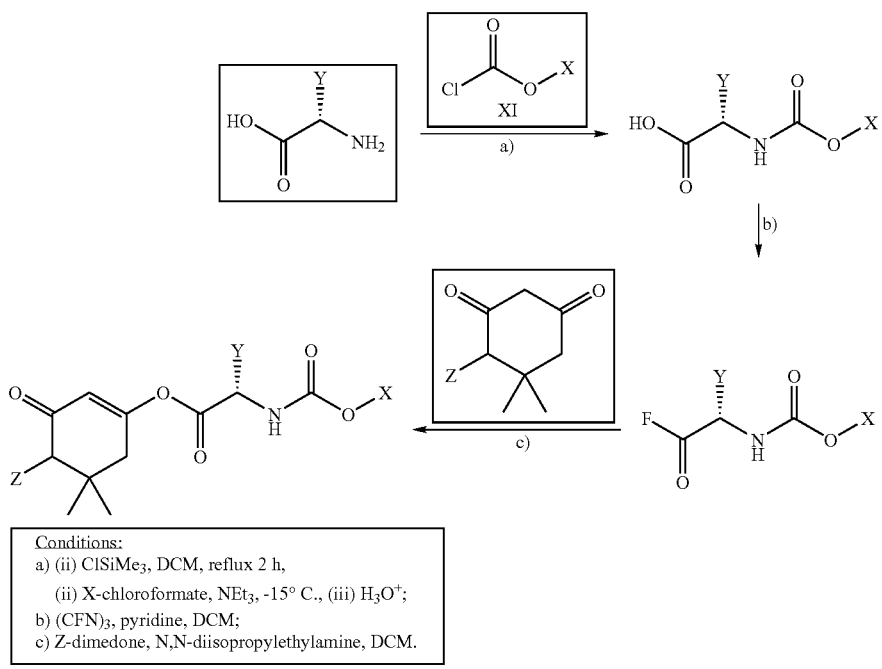

Scheme 1

Conditions:
a) (ii) ClSiMe$_3$, DCM, reflux 2 h,
   (ii) X-chloroformate, NEt$_3$, -15° C., (iii) H$_3$O$^+$;
b) (CFN)$_3$, pyridine, DCM;
c) Z-dimedone, N,N-diisopropylethylamine, DCM.

Variation of the N-protecting group may be achieved by reacting the free amino acid with a chloroformate, XI, using conditions described in Hartwig, W., Schöllkopf, U., Liebigs Ann. Chem., 1982, 1952–1970.

A fifth aspect of the invention relates to the use of a compound of the invention in the preparation of a medicament for use in the treatment of immunosuppressive disorders, parasite infections, rheumatoid arthritis, cancer or HIV-related disorders.

substrate of cyclophilin and detecting any change in the activity of cyclophilin on said known substrate.

A sixth aspect of the invention relates to a method of detecting the binding of a ligand to the PPIase binding site of cyclophilin, said method comprising the steps of:

(i) contacting a ligand with cyclophilin in the presence of a known substrate of cyclophilin; and (ii) detecting any change in the activity in the PPIase activity of cyclophilin on said known substrate;

and wherein said ligand is a compound according to the invention.

A seventh aspect of the invention provides a method of screening for a ligand capable of binding to a ligand binding domain of a cyclophilin, comprising:
(a) incubating a cyclophilin, a candidate compound and a compound of the invention;
(b) observing any change in the binding dissociation constant (Kd) as compared to the identical incubation lacking the candidate compound and, if the Kd has decreased,
(c) optionally preparing the candidate compound by conventional means.

An eighth aspect of the invention provides a method of screening for a ligand capable of binding to a ligand binding domain of a cyclophilin, comprising:
(a) incubating a cyclophilin with a candidate compound,
(b) generating a crystal of said cyclophilin and candidate compound and
(c) observing any interaction between the candidate compound and any of amino acids of the cyclophilin corresponding to Phe 113, Arg 55, Gln 111 and Asn 102 of cyclophilin A.

Preferably, said candidate compound is generated by conventional SAR modification of a compound of the invention.

As used herein, the term "conventional SAR modification" refers to standard methods known in the art for varying a given compound by way of chemical derivatisation.

The above methods may be used to screen for a ligand useful as an inhibitor of cyclophilin.

In the described methods the cyclophilin is preferably cyclophilin A, cyclophilin D or cyclophilin 40.

A ninth aspect of the invention relates to a process comprising the steps of:
(a) performing an assay method described hereinabove;
(b) identifying one or more ligands capable of binding to a ligand binding domain; and
(c) preparing a quantity of said one or more ligands.

A tenth aspect of the invention provides a process comprising the steps of:
(a) performing an assay method described hereinabove;
(b) identifying one or more ligands capable of binding to a ligand binding domain; and
(c) preparing a pharmaceutical composition comprising said one or more ligands.

An eleventh aspect of the invention provides a process comprising the steps of:
(a) performing an assay method described hereinabove;
(b) identifying one or more ligands capable of binding to a ligand binding domain;
(c) modifying said one or more ligands capable of binding to a ligand binding domain;
(d) performing the assay method described hereinabove;
(e) optionally preparing a pharmaceutical composition comprising said one or more ligands.

The invention also relates to a ligand identified by the method described hereinabove.

Yet another aspect of the invention relates to a pharmaceutical composition comprising a ligand identified by the method described hereinabove.

Another aspect of the invention relates to the use of a ligand identified by the method described hereinabove in the preparation of a pharmaceutical composition for use in the treatment of immunosuppressive disorders, parasite infections, rheumatoid arthritis, cancer or HIV-related disorders.

A further aspect of the invention relates to the use of an intermediate compound of formula VI

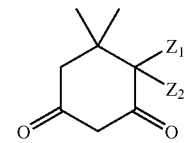

IV wherein $Z_1$ and $Z_2$ are defined as above, in the preparation of a medicament for use in the treatment of immunosuppressive disorders, parasite infections, rheumatoid arthritis, cancer or HIV-related disorders.

Preferably, said intermediate of formula IV is selected from the following:

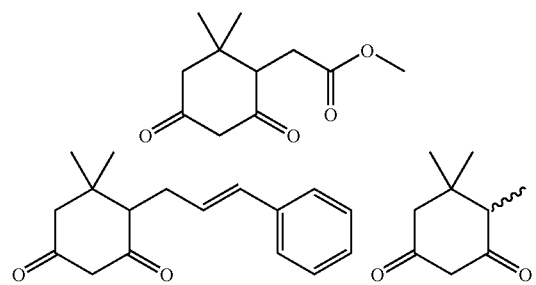

In another aspect, the invention further relates to the use of a compound of formula IX, X, XI or XII

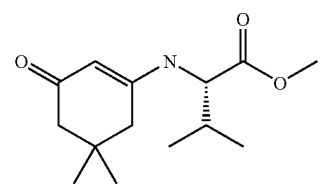

IX

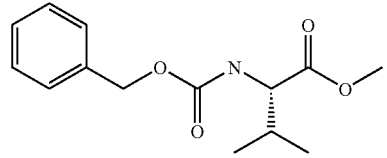

X

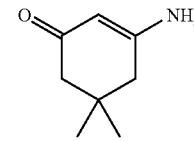

XI

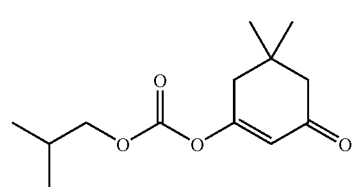

XII in the preparation of a medicament for use in the treatment of immunosuppressive disorders, parasite infections, rheumatoid arthritis, cancer or HIV-related disorders.

The invention also relates to the use of a compound of formula IV, IX, X, XI, or XII in an assay for determining binding to the PPIase binding site of cyclophilin. Another aspect of the invention relates to a complex comprising cyclophilin and a compound of formula IV, IX, X, XI or XII, and also to a pharmaceutical composition comprising a compound of formula IV, IX, X, XI or XII, together with a pharmaceutically acceptable diluent, excipient or carrier.

Yet another aspect of the invention relates to a method of detecting the binding of a ligand to the PPIase binding site of cyclophilin, as described hereinbefore, and wherein the ligand is a compound of formula IV, IX, X, XI or XII.

The present invention will now be described only by way of example, and with reference to the following figures, wherein:

FIG. 2 (lower trace) shows the mass spectrum for the complex of E11 bound to cyclophilin.

EXAMPLES

Figure 1:
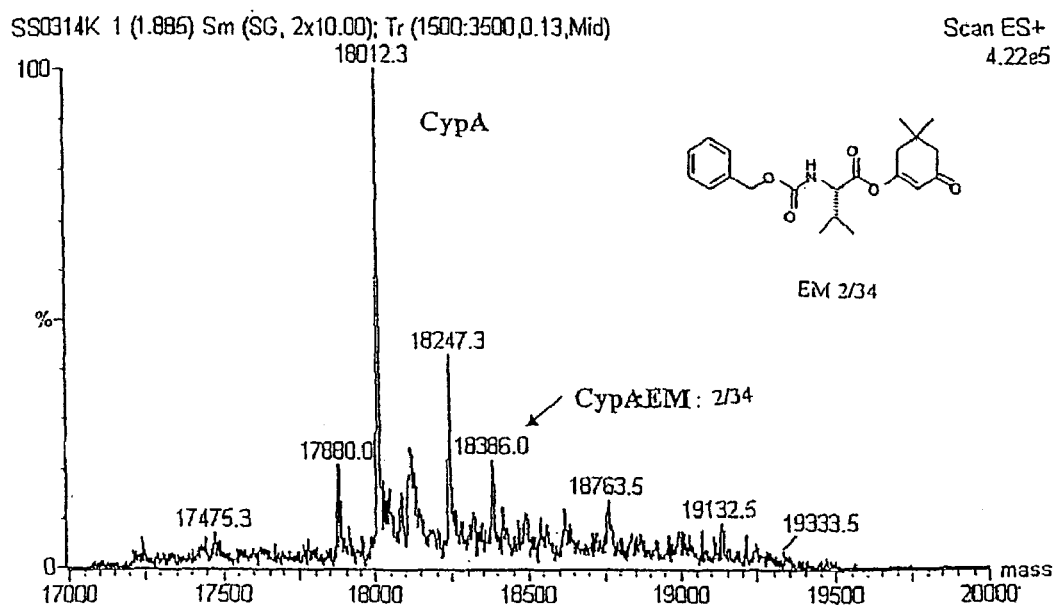
FIG. 1 shows an electrospray mass spectrum for the complex of compound EM2/34 bound to cyclophilin A.

Synthesis of Dimedone-Based Ligands for Cyclophilin A

Compounds of formula III were prepared according to scheme 2, shown below.

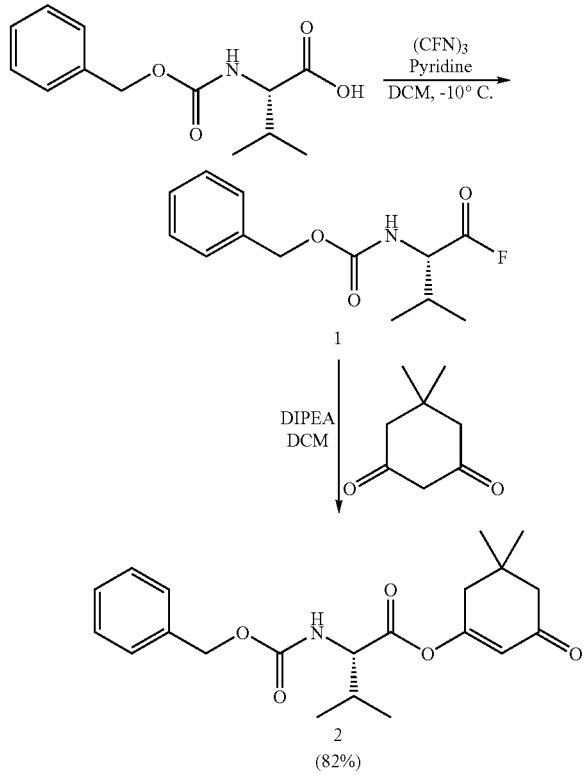

N-benzyloxycarbonyl-L-valinylfluoride (1)

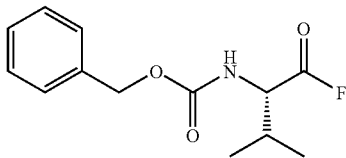

To a stirred solution of N-benzyloxycarbonyl-L-valine (0.50 g, 2.00 mmol) and pyridine (0.16 ml, 2.00 mmol) in anhydrous DCM (5 ml) kept under a $N_2$ atmosphere was added cyanuric fluoride (0.90 ml, 10.00 mmol) at −15 to −10° C. A white precipitate formed. The reaction was followed by TLC $CHCl_3$/MeOH/AcOH (9:1:0.1) on a small amount of reaction mixture quenched in MeOH. After 1 hr 40 min, crushed ice was added along with DCM (10 ml). The organic layer was separated and the aqueous layer extracted with DCM (5 ml). The combined DCM layers were washed with ice-cold water (10 ml), dried ($MgSO_4$) and concentrated under reduced pressure to afford a colourless oil (0.60 g, 119%) which was used in subsequent reactions without further purification: Rf=0.78 $CHCl_3$/MeOH/AcOH (9:1:0.1); $v_{max}$(polyethylene card) 3320 (N—H), 1843 (acid fluoride), 1738 (urethane, C═O), 1538 (amide II); $\delta_H$ (200 MHz, $CDCl_3$) 1.01 (3H, d, J 7.0, $CH(C^AH_3C^BH_3)$), 1.05 (3H, d, J 7.0, $CH(C^AH_3C^BH_3)$), 2.26 (1H, m, $CH(CH_3)_2$), 4.49 (1H, m, NHCH), 5.14 (3H, m, $OCH_2Ph$ & NH (masked)), 7.37 (5H, s, Ar—H); MS ES (+ve) found m/z 233.8 ($C_6H_5CH_2CONHCH(CH(CH_3)_2)$ CO—, 41%), 251.8 (N-Cbz-Val, 58), 268.9 (N-Cbz-$ValNH_4^+$, 64), 273.8 (N-Cbz-$ValNa^+$, 33), 289.9 (N-Cbz-$ValK^+$, 22), 341.9 (100), 502.1 (N-Cbz-Val dimer, 53), 507.1 ($M^+$ dimer, 55).

3-(N-benzyloxycarbonyl-L-valinyloxy)-5,5-dimethyl-2-cyclohexen-1-one (2): EM 2/34

To a stirred room temperature solution of N-benzyloxycarbonyl-L-valinylfluoride (1) (0.48 g, 1.89 mmol) in DCM (20 ml) was added dimedone (0.27 g, 1.89 mmol) and DIPEA (0.66 ml, 3.78 mmol). On addition of DIPEA there was an immediate colour change from colourless to green/brown then blue/purple. IR (crude solution; polyethylene disc) indicated disappearance of the acyl fluoride peak @1842 $cm^{-1}$. After stirring for ½ hr the solution was washed with 1N HCl (2×5 ml), saturated $NaHCO_3$ solution (2×5 ml), water (2×5 ml), dried ($MgSO_4$) and concentrated under reduced pressure to a blue/purple oil (0.62 g). Flash column chromatography on silica gel using $CHCl_3$/MeOH (9:1) as eluent afforded a pale yellow oil (0.58 g, 82%); $[\alpha]_D$ −15.6 (c 1.4, $CHCl_3$); Rf=0.75 $CHCl_3$/MeOH (9:1); $v_{max}$(NaCl) 3326 br (N—H), 1769 (vinyl ester), 1715 (urethane, C═O), 1668 (α,β-unsaturated ketone), 1532 (amide II); $\delta_H$ (250 MHz, CDCl$_3$) 0.95 (3H, d, J 7.0, CH(C$^A$H$_3$C$^B$H$_3$)), 1.02 (3H, d, J 7.0, CH(C$^A$H$_3$C$^B$H$_3$)), 1.10 (6H, s, C(CH$_3$)$_2$), 2.20–2.27 (1H, m, CH(CH$_3$)$_2$), 2.27 (2H, s, CH$_2$C(CH$_3$)$_2$), 2.39 (2H, s, CH$_2$C(CH$_3$)$_2$), 4.39 (1H, dd, J 9.0, 5.0, NHCH), 5.12 (2H, s, OCH$_2$Ph), 5.19 (1H, d, J 9.0, NH), 5.89 (1H, s, COCH=CO), 7.35 (5H, s, Ar—H); $\delta_C$ (63 MHz, DEPT, CDCl$_3$) 17.5 (CH(C$^A$H$_3$C$^B$H$_3$)), 18.9 (CH (C$^A$H$_3$C$^B$H$_3$)), 27.9 (C(C$^A$H$_3$C$^B$H$_3$)), 28.0 (C(C$^A$H$_3$C$^B$H$_3$)), 30.9 (CH(CH$_3$)$_2$), 33.1 (C(CH$_3$)$_2$), 41.8 (CH$_2$C(CH$_3$)$_2$), 50.7 (CH$_2$C(CH$_3$)$_2$), 59.1 (NHCH), 67.2 (OCH$_2$Ph), 116.8 (COCH=CO), [128.0 (CH), 128.2 (CH), 128.5 (CH), 5C, Ar—H], 135.9 (OCH$_2$Ph), 156.1 (CONH), 167.7 (COOC=CH), 169.1 (NHCHCO), 199.0 (COCH=COCO); MS ES (+ve) found m/z 396.0 (MNa$^+$, 100%), 437.1 (22); HRMS FAB (+ve) found m/z 374.19741 (MH$^+$), C$_{21}$H$_{28}$NO$_5$ requires 374.19675.

N-benzyloxycarbonyl-L-leucinylfluoride (3)

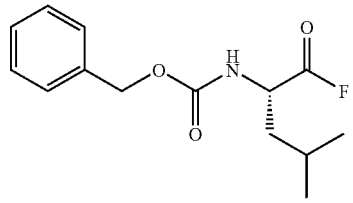

To a stirred solution of N-benzyloxycarbonyl-L-leucine (0.50 g, 1.87 mmol) and pyridine (0.15 ml, 1.88 mmol) in anhydrous DCM (5 ml) kept under a N$_2$ atmosphere was added cyanuric fluoride (0.51 ml, 5.64 mmol) at −15 to −10° C. A white precipitate formed. After stirring for 1 hr at −5° C., IR of the crude reaction mixture indicated formation of the acyl fluoride. After 2 hrs crushed ice was added along with DCM (10 ml). The organic layer was separated and the aqueous layer extracted with DCM (5 ml). The combined DCM layers were washed with ice-cold water (10 ml), dried (MgSO$_4$) and concentrated under reduced pressure to afford a colourless oil (0.36 g, 73%) which was used in subsequent reactions without further purification: $v_{max}$(polyethylene card) 3317 (N—H), 1843 (acid fluoride); $\delta_H$ (200 MHz, CDCl$_3$) 0.97 (6H, d, J 6.0, CH(CH$_3$)$_2$), 1.62–1.78 (3H, m, CH(CH$_3$)$_2$ & CH$_2$CH(CH$_3$)$_2$), 4.54–4.61 (1H, m, NHCH), 5.02 (1H, m, NH), 5.14 (2H, s, CH$_2$Ph), 7.36 (5H, s, Ar—H).

3-(N-benzyloxycarbonyl-L-leucinyloxy)-5,5-dimethyl-2-cyclohexen-1-one (4): EM 3/26/2/5

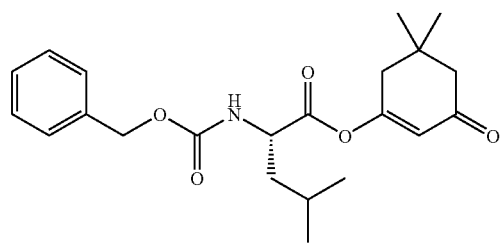

Method A

N-Benzyloxycarbonyl-L-leucinylfluoride (3) (0.36 g, 1.36 mmol) in DCM (15 ml) was stirred at room temperature with dimedone (0.19 g, 1.36 mmol) and DIPEA (0.47 ml, 2.72 mmol). The solution changed colour from pale yellow to blue/purple. After 20 min IR (crude mixture; polyethylene disc) indicated disappearance of the acyl fluoride. The solution was washed with 2N HCl (2×5 ml), saturated NaHCO$_3$ solution (2×5 ml), water (2×5 ml), dried (MgSO$_4$) and concentrated under reduced pressure to yield a blue/purple oil (0.42 g). Flash column chromatography on silica gel using cyclohexane/diethyl ether (1:1) as eluent afforded a colourless oil (0.16 g, 29%); [α]$_D$−18.0 (c 2.2, CHCl$_3$); Rf=0.33 cyclohexane/diethyl ether (1:1); $v_{max}$(polyethylene card) 3322 (N—H), 1770 (vinyl ester), 1715 (urethane, C=O), 1674 (α,β-unsaturated ketone), 1532 (amide II); $\delta_H$ (250 MHz, CDCl$_3$) 0.96 (6H, d, J 6.0, CH(CH$_3$)$_2$), 1.06 (6H, s, C(CH$_3$)$_2$), 1.58–1.76 (3H, m, CH$_2$CH(CH$_3$)$_2$), 2.25 (2H, s, CH$_2$C(CH$_3$)$_2$), 2.38 (2H, s, CH$_2$C(CH$_3$)$_2$), 4.42–4.46 (1H, m, CHNH), 5.11 (2H, s, CH$_2$Ph), 5.21 (1H, d, J 8.0, NH), 5.90 (1H, s, COCH=CO), 7.33 (5H, s, Ar—H); $\delta_C$ (63 MHz, DEPT, CDCl$_3$) 21.5 (CH(C$^A$H$_3$C$^B$H$_3$)), 22.7 (CH (C$^A$H$_3$C$^B$H$_3$)), 24.7 (CH(CH$_3$)$_2$), 27.9 (C(C$^A$H$_3$C$^B$H$_3$)), 28.0 (C(C$^A$H$_3$C$^B$H$_3$)), 33.0 (C(CH$_3$)$_2$), 40.9 (CH$_2$CH(CH$_3$)$_2$), 41.7 (CH$_2$C(CH$_2$)$_2$), 50.6 (CH$_2$C(CH$_3$)$_2$), 52.6 (NHCH), 67.1 (OCH$_2$Ph), 116.1 (COCH=COCH$_2$), [127.9 (CH), 128.2 (CH), 128.4 (CH), 5C, Ar—H], 135.9 (OCH$_2$Ph), 155.8 (OCONH), 167.8 (COOC=CH), 170.0 (NHCHCO), 199.2 (COCH=COCO); MS ES (+ve) found m/z 410.2 (MNa$^+$, 100%), 426.0 (MK$^+$, 17), 433.3 (17), 451.2 (48); HRMS FAB (+ve) found m/z 388.21214 (MH$^+$), C$_{22}$H$_{30}$NO$_5$ requires 388.21240.

Method B

To a cold (−10° C.) solution of N-benzyloxycarbonyl-L-leucine (0.73 g, 2.74 mmol) in EtOH (5 ml), were added triethylamine (0.38 ml, 2.74 mmol), and ethyl chloroformate (0.26 ml, 2.74 mmol). The mixture was stirred for 15 min at −5° C., and dimedone (0.38 g, 2.74 mmol) added. After stirring for 1 hr 20 min at 0° C., TLC hexane/EtOAc (1:1) indicated formation of products. The reaction was allowed to warm to room temperature and stirred for 1 hr before concentration under reduced pressure to give a colourless oil (1.66 g). Flash column chromatography on silica gel using hexane/EtOAc (4:1→2:1) yielded a colourless oil (0.34 g, 32%). Analysis identical to (4).

EM 3/26/2/5 was prepared via the acid fluoride (Method A) and via the mixed anhydride (Method B).

EM 3/26/1/2 was prepared using Method B.

1-(4,4-dimethyl-2,6-dioxocyclohexylidene)-2-benzyloxycarbonylamino-3-methylbutanol (5): EM 3/11/1

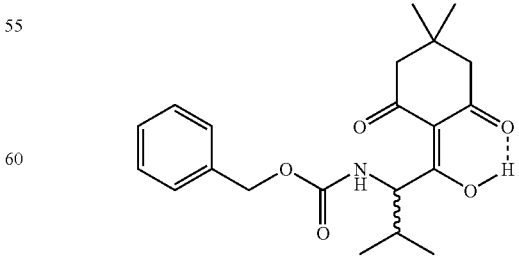

The enol ester (2) (0.56 g, 1.50 mmol) was dissolved in MeCN (8 ml) containing triethylamine (0.84 ml, 6.00 ml)

and acetone cyanohydrin (14 μl, 0.15 mmol). After 2.5 hrs, TLC hexane/EtOAc (1:1) indicated remaining enol ester (2). The solution was stirred at room temperature overnight then partitioned between hexane (8 ml) and cold 1N HCl (8 ml). The hexane phase was washed with water (2 ml), dried (MgSO$_4$) and concentrated under reduced pressure to yield an off-white solid (0.26 g, 66%): mp 72° C.; [α]$_D$+12.4 (c 2.1, CHCl$_3$); Rf=0.41 hexane/EtOAc (1:1); ν$_{max}$ (KBr) 3424 (O—H & N—H), 1722 (urethane, C=O), 1667 (α,β-unsaturated ketone), 1513 (amide II); δ$_H$ (200 MHz, CDCl$_3$) 0.75 (3H, d, J 7.0, CH(C$^A$H$_3$C$^B$H$_3$)), 0.86–1.27 (9H, m, CH(C$^A$H$_3$C$^B$H$_3$) & C(CH$_3$)$_2$), 2.07–2.13 (1H, m, CH(CH$_3$)$_2$), 2,28–2.35 (2H, m, CH$_2$C(CH$_3$)$_2$), 2.54 (2H, s, CH$_2$C(CH$_3$)$_2$), 5.08 (2H, s, CH$_2$Ph), 5.49 (1H, d, J 9.5, NH), 5.60 (1H, dd, J 9.5, 3.0, CHCH(CH$_3$)$_2$), 7.34 (5H, s, Ar—H), 17.54 (1H, s, Oh); δ$_C$ (63 MHz, DEPT, CDCl$_3$) 15.6 (CH (C$^A$H$_3$C$^B$H$_3$)), 20.3 (CH(C$^A$H$_3$C$^B$H$_3$)), 27.7 (C(C$^A$H$_3$C$^B$H$_3$)), 28.3 (C(C$^A$H$_3$C$^B$H$_3$)), 30.6 (CH(CH$_3$)$_2$), 45.9 (CH$_2$C(CH$_3$)$_2$), 52.2 (CH$_2$C(CH$_3$)$_2$), 60.9 (CHCH (CH$_3$)$_2$), 66.8 (CH$_2$Ph), 110.8 (C=COH), [128.0 (CH), 128.4 (CH), 5C, Ar—H], 136.3 (OCH$_2$Ph), 156.2 (OCONH), [194.4 (C), 196.7 (C), 203.5 (C), COC=C(OH) CO]; MS ES (+ve) found m/z 373.9 (MH$^+$, 90%), 396.0 (MNa$^+$, 100); HRMS FAB (+ve) found m/z 374.19769 (MH$^+$), C$_{21}$H$_{28}$NO$_5$ requires 374.19675.

N-[1-(4,4-dimethyl-2,6-dioxocyclohexylidene)-2-benzyloxycarbonylamino-3-methylbutyl]phenylalanine methyl ester (6): EM 2/40

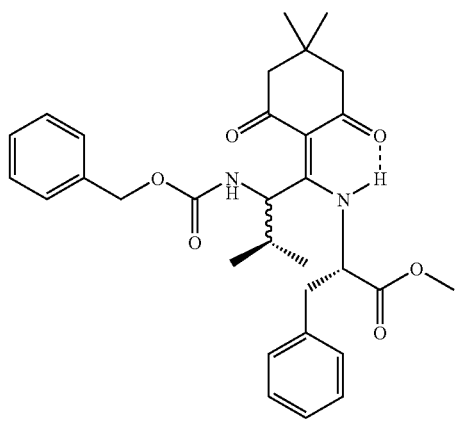

(diastereomers in ratio 60:40, X:Y)

1-(4,4-dimethyl-2,6-dioxocyclohexylidene)-2-benzyloxycarbonylamino-3-methyl-butanol (5) (0.11 g, 0.29 mmol) was dissolved in DMF (1 ml). L-phenylalanine methyl ester HCl salt (0.06 g, 0.29 mmol) was added followed by DIPEA (0.05 ml, 0.29 mmol) and the mixture stirred at room temperature overnight after which time TLC hexane/EtOAc (1:1) indicated remaining (5). The reaction was heated at 50° C. for 7 hrs before removal of the solvent under reduced pressure to yield a yellow oil (0.19 g). Flash column chromatography using hexane/EtOAc (1:1) as eluent afforded a colourless oil (0.05 g, 34%); [α]$_D$–30.5 (c 2.5, CHCl$_3$); Rf=0.64 hexane/EtOAc (1:1); ν$_{max}$(polyethylene card) 3352 (N—H), 1748 (ester), 1713 (urethane, C=O), 1634 (α,β-unsaturated ketone), 1565 (amide II); δ$_H$ (360 MHz, COSY, CDCl$_3$) 0.33 (3H, d, J 7.0, CH(C$^A$H$_3$C$^B$H$_3$), Y), 0.76 (3H, d, J 7.0, CH(C$^A$H$_3$C$^B$H$_3$), X), 0.92 (3H, d, J 6.5, CH(C$^A$H$_3$C$^B$H$_3$), Y), 1.01 (3H, d, J 6.5, CH(C$^A$H$_3$C$^B$H$_3$), X), 1.04–1.07 (12H, m, C(CH$_3$)$_2$, X & Y), 2.02–2.11 (1H, m, CH(CH$_3$)$_2$, Y), 2.19–2.26 (1H, m, CH(CH$_3$)$_2$, X), 2.30–2.52 (8H, m, CH$_2$C(CH$_3$)$_2$CH$_2$, X & Y), 3.17 (1H, dd, J 14.0, 9.0, CHCH$_A$H$_B$Ph, Y), 3.29 (2H, d, J 7.0, CHCH$_2$Ph, X), 3.40 (1H, dd, J 14.0, 4.5, CHCH$_A$H$_B$ Ph, Y), 3.69 (3H, s, OCH$_3$, Y), 3.72 (3H, s, OCH$_3$, X), 4.30 (1H, dd, J 10.5, 10.5, CHCH(CH$_3$)$_2$, Y), 4.48 (1H, dd, J 10.5, 10.5, CHCH(CH$_3$)$_2$, X), 5.05–5.19 (5H, m, OCH$_2$Ph, X & Y, CHCH$_2$Ph, Y), 5.37 (1H, dt, J 8.0, 7.0, CHCH$_2$Ph, X), 7.22–7.39 (20H, m, Ar—H, X & Y), 7.69 (1H, d, J 12.5, CONH, Y), 7.72 (1H, d, J 10.5, CONH, X), 14.61 (1H, d, J 8.0, COCHNH, Y), 14.71 (1 h, d, J 8.0, COCHNH, X); δ$_C$ (63 MHz, DEPT, CDCl$_3$) 19.2 (CH(C$^A$H$_3$C$^B$H$_3$), Y), 19.3 (2C, CH(C$^A$H$_3$C$^B$H$_3$), X & Y), 19.9 (CH(C$^A$H$_3$C$^B$H$_3$), X), 27.4 (C(C$^A$H$_3$C$^B$H$_3$), Y), 27.5 (C(C$^A$H$_3$C$^B$H$_3$), X), 28.5 (C(C$^A$H$_3$C$^B$H$_3$), X), 28.6 (C(C$^A$H$_3$C$^B$H$_3$), Y), 29.1 (CH (CH$_3$)$_2$, Y), 29.4 (CH(CH$_3$)$_2$, X), 29.8 (2C, C(CH$_3$)$_2$, X & Y), 39.3 (CHCH$_2$Ph, Y), 39.8 (CHCH$_2$Ph, X), 52.0 (CH$_2$C (CH$_3$)$_2$, X), 52.1 (CH$_2$C(CH$_3$)$_2$, Y), 52.4 (OCH$_3$, X), 52.7 (OCH$_3$, Y), (2C, CH$_2$C(CH$_3$)$_2$, X & Y), 55.8 (CHCH(CH$_3$)$_2$, Y), 56.1 (CHCH(CH$_3$)$_2$, X), 59.1 (CHCH$_2$Ph, X), 59.7 (CHCH$_2$Ph, Y), 66.5 (OCH$_2$Ph, Y), 66.6 (OCH$_2$Ph, X), 107.0 (COC=CNH, X), 107.2 (COC=CNH, Y), [127.2 (CH), 127.3 (CH), 127.6 (CH), 127.7 (CH), 127.9 (CH), 128.0 (CH), 128.2 (CH), 128.3 (CH), 128.4 (CH), 128.6 (CH), 129.2 (CH), 129.3 (CH), 20C, Ar—H, X & Y), 134.5 (CHCH$_2$Ph, X), 135.2 (CHCH$_2$Ph, Y), 136.4 (OCH$_2$Ph, X), 136.5 (OCH$_2$Ph, Y), 156.4 (2C, OCONH, X & Y), 169.8 (COC=CNH, Y), 169.9 (COC=CNH, X), 173.0 (COOCH$_3$, X), 173.6 (COOCH$_3$, Y), 197.2 (2C, COC=CNH, X & Y), 200.3 (2C, COC=CNH, X & Y); MS ES (+ve) found m/z 535.2 (MH$^+$, 29%), 557.1 (MNa$^+$, 100); HRMS FAB (+ve) found m/z 535.28083 (MH$^+$), C$_{31}$H$_{39}$N$_2$O$_6$ requires 535.28081.

EM 3/29/1/1

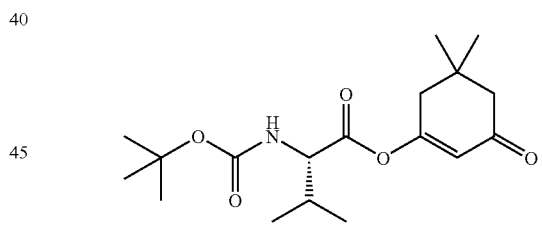

To a cold (−10° C.) solution of tert-butyloxycarbonyl-L-valine (5.0 g, 23.0 mmol) in THF (50 ml), were added triethylamine (3.21 ml, 23.0 mmol), and methyl chloroformate (1.96 ml, 25.0 mmol). A white precipitate formed and further THF (30 ml) was added. The mixture was stirred for 5 min at −5° C., and dimedone (3.22 g, 23.0 mmol) added. The reaction was allowed to warm to room temperature and stirring continued overnight. The reaction mixture was diluted with EtOAc (100 ml), washed with brine (3×50 ml), dried over MgSO$_4$ and concentrated under reduced pressure to a colourless oil (4.48 g). Flash column chromatography on silica gel using hexane/EtOAc (3:2) yielded a colourless oil (0.29 g, 37%); Rf=0.49 hexane/EtOAc (3:2); δ$_H$ (250 MHz, CDCl$_3$) 0.92 (3H, d, J 7.0, CH(C$^A$H$_3$C$^B$H$_3$)), 0.99 (3H, d, J 7.0, CH(C$^A$H$_3$C$^B$H$_3$)), 1.07 (6H, s, C(CH$_3$)$_2$), 1.41 (9H, s, C(CH$_3$)$_3$), 2.16–2.21 (1H, m, CH(CH$_3$)$_2$), 2.24 (2H, s, CH$_2$C(CH$_3$)$_2$), 2.38 (2H, s, CH$_2$C(CH$_3$)$_2$), 4.26 (1H, dd, J 9.0, 5.0, NHCH), 4.99 (1H, d, J 9.0, NH), 5.87 (1H, s, COCH=CO); $\delta_C$ (63 MHz, DEPT, CDCl$_3$) 17.5 (CH (C$^A$H$_3$C$^B$H$_3$)), 18.9 (CH(C$^A$H$_3$C$^B$H$_3$)), 28.0 (C(CH$_3$)$_2$), 28.1 (C(CH$_3$)$_3$), 30.8 (CH(CH$_3$)$_2$), 33.0 (C(CH$_3$)$_2$), 41.8 (CH$_2$C (CH$_3$)$_2$), 50.6 (CH$_2$C(CH$_3$)$_2$), 58.7 (NHCH), 80.1 (C(CH$_3$)$_3$), 116.6 (COCH=CO), 155.5 (CONH), 167.8 (COOC=CH), 169.3 (NHCHCO), 199.1 (COCH=COCO).

EM 3/22/1

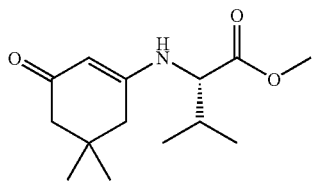

Prepared in accordance to the procedure reported by Halpern, B.; James, L. B., Aust. J. Chem., 1964, 17, 1282–1287.

To a solution of dimedone (1.00 g, 7.1 mmol) in CHCl$_3$ (20 ml) was added L-valine methyl ester. HCl salt (1.20 g, 7.1 mmol) and the suspension neutralised by the addition of triethylamine (1.0 ml, 7.1 mmol). The resulting solution was stirred at room temperature overnight. The solution was then concentrated under reduced pressure to a yellow residue, which was triturated with hot ether, filtered and washed with ether to yield a white solid (1.66 g). The solid was dissolved in CHCl$_3$, washed with 2N HCl and dried (MgSO$_4$) before concentration under reduced pressure to a colourless residue (1.02 g, 57%); Rf=0.44 DCM/MeOH (9:1); $\delta_H$ (200 MHz, CDCl$_3$) 0.92 (3H, d, J 7.0, CH(C$^A$H$_3$C$^B$H$_3$)), 0.94 (3H, d, J 7.0, CH(C$^A$H$_3$C$^B$H$_3$)), 1.06 (6H, s, C(CH$_3$)$_2$), 1.82–1.95 (1H, m, CH(CH$_3$)$_2$), 2.17 (2H, s, CH$_2$C(CH$_3$)$_2$), 2.23 (2H, s, CH$_2$C(CH$_3$)$_2$), 3.91 (1H, dd, J 8.0, 5.0, NHCH), 4.88 (1H, d, J 8.0 , NH), 5.06 (1H, s, COCH=CO); MS ES (+ve) found m/z 253.9 (MH$^+$, 100%), 276.1 (MNa$^+$, 16%) 317.0 (MNa$^+$MeCN, 64%).

EM 3/27

This compound was prepared in accordance to the procedure described by Dendrinos, K. G.; Kalivretenos, A. G., J Chem Soc, Perkin Trans 1, 1998, 9, 1463–1464.

The route shown in Scheme 2 can be extended to incorporate 4-alkyl dimedone derivatives, as shown in Scheme 3 below. 4-Alkyl dimedone derivatives such as EM 4/33/1 may be prepared in accordance with the method described by Berry, N. M., Darey, M. C. P., Harwood, L. M., Synthesis Commun., 1986, 476–480.

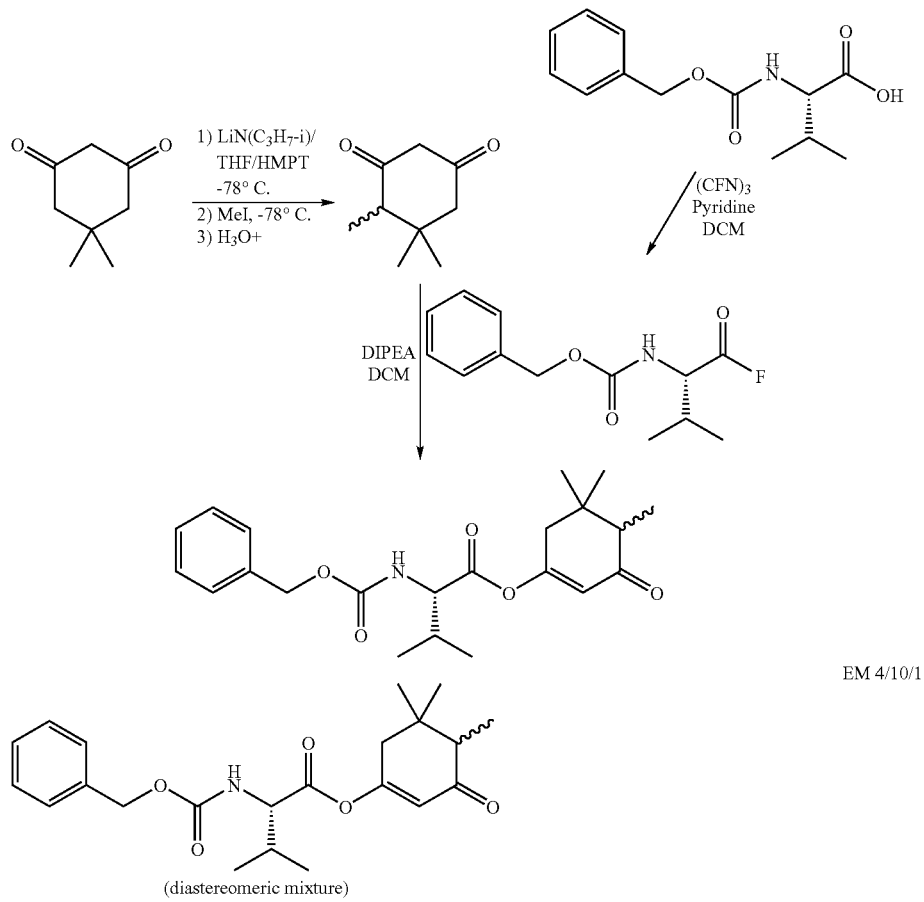

N-benzyloxycarbonyl-L-valine (0.20 g, 0.8 mmol) was dissolved in anhydrous DCM (2 ml) and the solution cooled to −10° C. Pyridine (0.06 ml, 0.8 mmol) and cyanuric fluoride (0.2 ml, 2.3 mmol) were added and the solution went orange/yellow. After stirring for 0.5 h, TLC DCM/MeOH (9:1) indicated formation of product. Crushed ice was added along with DCM. The aqueous layer was extracted with 2× DCM and the combined organic layers washed with ice-water and dried over MgSO$_4$. The solution was concentrated under reduced pressure to a colourless liquid (0.14 g), which was used in the next step without further purification. The liquid was dissolved in DCM (2 ml) and EM 4/33/1 (0.09 g, 0.6 mmol) added, followed by DIPEA (0.10 ml, 0.6 mmol). The resulting orange/red solution was stirred overnight at room temperature, after which time a blue/pink colour was observed. TLC indicated complete reaction of EM 4/33/1. The solution was concentrated under reduced pressure to a blue/pink oil. Flash column chromatography on silica gel using DCM/MeOH (9:1) yielded a colourless oil (0.17 g, 78%); Rf=0.83 DCM/MeOH (9:1); $\delta_H$ (250 MHz, CDCl$_3$) 0.92 (3H, d, J 7.0, CH(C$^A$H$_3$C$^B$H$_3$)), 0.99 $\delta_H$ (250 MHz, CDCl$_3$) 0.93–1.11 (155H, m, CH(CH$_3$)$_2$, C(CH$_3$)$_2$CH(CH$_3$)), 2.19–2.58 (4H, m, CH(CH$_3$)$_2$, CH$_2$C(CH$_3$)$_2$CH(CH$_3$), 4.38 (1H, dd, J 9.0, 5.0, NHCH), 5.11 (2H, s, OCH$_2$Ph), 5.25 (1H, d, J 9.0, NH), 5.85 (1H, s, COCH=CO), 7.35 (5H, s, Ar—H); $\delta_C$ (63 MHz, DEPT, CDCl$_3$) 9.4 (COCHCH$_3$), 17.4 (CH(C$^A$H$_3$C$^B$H$_3$)), 18.9 (CH(C$^A$H$_3$C$^B$H$_3$)), 22.0 (C(C$^A$H$_3$C$^B$H$_3$)), 28.4 (C(C$^A$H$_3$C$^B$H$_3$)), 31.0 (CH(CH$_3$)$_2$), 35.9 (C(CH$_3$)$_2$), 41.9 (CH$_2$C(CH$_3$)$_2$), 51.3 (COCHCH$_3$), 59.0 (NHCH), 67.1 (OCH$_2$Ph), 116.3 (COCH=CO), [128.0 (CH), 128.2 (CH), 128.5 (CH), 5C, Ar—H], 135.9 (OCH$_2$Ph), 156.1 (CONH), 166.2 (COOC=CH), 169.1 (NHCHCO), 201.7 (COCH=COCO); MS ES (+ve) found m/z 387.9 (MH$^+$, 20%), 404.9 (MNH$_4^+$, 51%), 410.04 (MNa$^+$, 100%); HRMS FAB (+ve) found m/z 388.21228 (MH$^+$), C$_{22}$H$_{29}$NO$_5$ requires 388.21240.

Crystallisation and Structure Determination

Recombinant human cyclophilin A was concentrated to 14 mg/ml in Hepes 20 mM, NaCl 100 mM and NaN3 0.02% (w/v). Crystals of the CyP-A were grown by vapour diffusion at 17° C. by the hanging drop method. The precipitating solution in the well consisted of 100 mM Tris.HCl (pH 8.0), 22% (w/v) PEG 8000, 5% (v/v) DMSO, 0.02% NaN$_3$. The initial 8 ml drop consisted of 50 mM Tris.HCl (pH 8.0), 11% (w/v) PEG 8000, 2.5% (v/v) DMSO, 0.02% NaN3, 0.4mM CyP-A.

The ligand was introduced into crystals of native human cyclophilin A that had grown to approximately 0.2 mm×0.1 mm×0.1 mm. The native crystals were then transferred into solutions containing the ligand of interest at between 20 mM and 100 mM. The crystal was soaked for between 10 and 20 minutes before transferring it briefly (20 seconds) to a cryopectant solution consisting of 100 mM Tris.HCL (pH8.0), 22% w/v PEG8000, 26% glycerol. The crystal was then flash frozen by plunging into liquid nitrogen.

Data was collected using a Nonius rotating anode generator. The resolution of the data was improved when the same crystal was collected at Daresbury SRS (1=1.488) Data sets were processed with DENZO and scaled with SCALEPACK.

The X-ray structures of three ligand complexes have been solved and (partially) refined (formulae shown below, and data shown in Table 1). The X-ray structures unambiguously show each ligand binding to the active site of human cyclophilin A and provide useful information about which features are important for binding and also which new derivatives are likely to produce better binding.

TABLE 1

| Structure | unit cell (A) | Resolution (A) | Space group | unique reflections | Rmerge (%) | completeness | Rfactor |
|---|---|---|---|---|---|---|---|
| Cyp-EM2/34 | a 42.3 | 1.8 | P212121 | 17826 | 7.1 | 97.5% | 20.4% |
|  | b 52.8 |  |  |  |  |  |  |
|  | c 89.6 |  |  |  |  |  |  |
| Cyp-EM4/33/1 | a 42.9 | 1.8 | P212121 | 15569 | 10.1 | 85.5% | 22.8% |
|  | b 54.2 |  |  |  |  |  |  |
|  | c 88.9 |  |  |  |  |  |  |
| Cyp-EM4/10/1 | a 42.4 | 2.3 | P212121 | 6864 | 10.4 | 95.5% | 18.99% |
|  | b 52.4 |  |  |  |  |  |  |
|  | c 88.7 |  |  |  |  |  |  |

EM2/34

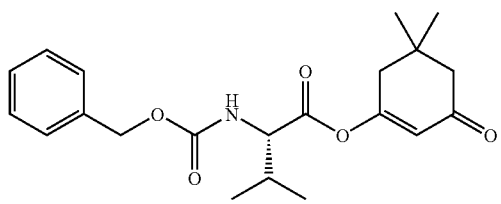

EM4/33/1

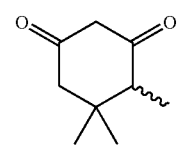

TABLE 1-continued

| Structure | unit cell (A) | Resolution (A) | Space group | unique reflections | Rmerge (%) | completeness | Rfactor |
|---|---|---|---|---|---|---|---|
| EM4/10/1 | | | | | | | |

Mass Spectroscopy Studies

Figure 2:
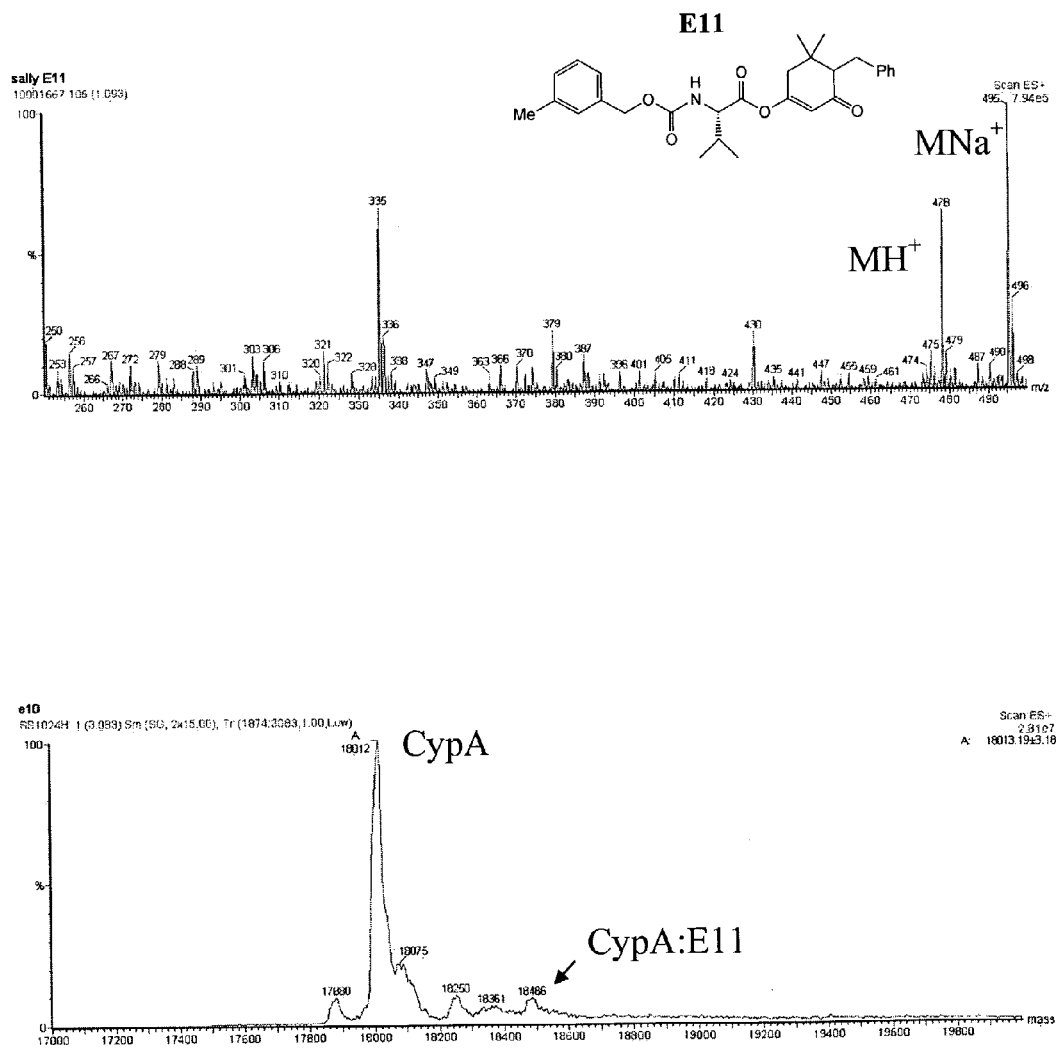
FIG. 2 (upper trace) show the electrospray mass spectrum for compound E11.

Further characterisation studies on the EM2/34-cyclophilin A complex were carried out using electrospray mass spectrometry. The results are shown in FIGS. 1 and 2.

Protein and Inhibitors

Cyclophilin A was obtained from Novartis AG. Cyclosporin was obtained from Sigma. Cyclosporin analogues were obtained from Mutter in Switzerland. Ammonium acetate was obtained from Sigma.

Electrospray Ionisation Mass Spectrometry (ESI-MS)

ESI mass spectra were recorded on a Micromass Platform II mass spectrometer equiped with an electrospray interface and operated in postive-ion mode. The quadrupole had an extended range to 4000 m/z. Data was acquired over 500 m/z to 3500 m/z range (unless otherwise indicated) with a scan time of 15 s. The capillary voltage was 3.5 kV, the counter electrode 0.5 kV, the cone voltage 50 V, the skimmer offset 5V. The source temperature was maintained at 65° C. The nebuliser and bath gases were nitrogen delivered at flow rates of 30 and 300 l/h, respectively.

All samples were introduced using a Harvard Apparatus infusion pump, at a rate of 8 µl/min.

Protein Preparation

The cyclophilin protein was made in 50 mM Hepes, 5 mM β mercaptamethanol, 0.1 mM NaCl. 1 ml of 13 mg/ml (by Bradford assay). This was dialysed against 2–3 liters of 10 mM ammonium acetate, pH 6.8, adjusted by ammonia. The dialysed sample was then diluted to a stock of 100 µM cyclophilin concentration for use in experiments. The protein concentration for experiments was 20 µM unless otherwise specified.

Inhibitor Preparation

The inhibitors were made up to 1 mM in methanol and then diluted to 10 µM in ammonium acetate. The final concentration of the inhibitor in solution was 20 µM.

Binding Affinity Studies and the E11-cyclophilin complex.

Binding constants measuring the affinity of selected compounds of the invention are shown below in Table 2. In each case, the binding constant was measured by means of a fluorescence assay, for example as disclosed by Husi, H. and Zurini, M. G. M. [Comparative binding studies of cyclophilins to cyclosporin-A and derivatives by fluorescence measurements, Analytical Biochemistry, 1994, 222, 251–255].

Fluorescence Assay: Interaction with Cyclophilin A

The dissociation constant (Kd) for a number of ligands has been was obtained by fluorescence measurements. Cyclophilin A has only one tryptophan, located about 8 Å from the centre of the active site making a hydrogen bond to the inhibitor cyclosporin when bound. After each addition of ligand, the portion of the protein bound is proportional to the fractional fluorescence change. Measurements were carried out using a Perkin Elmer LS50B fluorescence spectrophotometer. The experiments took place at 20° C. Constant temperature was maintained within the cuvette by a temperature control. The protein solution was equilibrated until the signal was stable. A 1.4 ml fluorescence cuvette was used (Hellma 6140F). The excitation wavelength was 280 nm and the emission wavelength was varied from 330 to 345 nm according to protein and ligand. Emission and excitation slits varied from 2.5 to 10 nm, determined by experimental parameters.

The Kd (dissociation constant) has been estimated by assuming a 50% occupancy of the protein at fractional fluorescence change of 50%. At this point the concentration of the bound ligand equals the free protein. For each ligand concentration one fluorescence value was measured, and at the same concentrations a reference emission value was taken. The difference between the two values was calculated and a new corrected value was used to determine the Kd graphically.

Cyp-A solutions of 5 to 0.5 mM in 50 mMTris, 100 mM NaCl, pH=7.4 were used. Protein concentration varied according to the ligand under test.

Enzymatic Assay

PPIase activity is assessed with the α-chymotrypsin-coupled enzymatic assay [Determination of kinetic constants for peptidyl cis-trans isomerase by an improved spectrophotometric assay (1 991); Kofron J L, Kuzmic P, Kishore V, Colon-Bonilla E and Rich D., Biochemistry 30, 6127–6134]. α-Chymotrypsin selectively hydrolyses the C-terminal p-nitroanilide bond of the substrate in the trans X-Pro conformer only. This hydrolysis releases a chromophore 4-nitroaniline, the accumulation of which is recorded by measuring the absorbance at 400 nm as a function of time. The trans peptide is cleaved within the deadtime so this cleavage does not contribute to the total reaction time. Substrate (stock solution of 100 mM) was dissolved in LiCl/TFE. The experiment took place at 4° C. Constant temperature was maintained within the cuvette by a Peltier (PTP-1) temperature control unit. A mini magnetic stirring system (telemoduel from Variomag)) was used for mixing the solution in the cuvette after the addition of the substrate. A Perkin Elmer UV/VIS Lambda 20 spectrophotometer was used.

The following materials were used:
Substrate: Suc-Ala-Ala-Pro-pNA (Bachem AG) (N-succinyl-Ala-Ala-Pro-Phe-pnitroanilide)
Proteins: Cyp-A solution was freshly prepared before the experiment from frozen stock solution, at the appropriate concentration by dilution in buffer 50 mM Hepes, 100 mM NaCl pH=8.0. α-chymotrypsin (Sigma)

In a typical experiment 90 μl of 2.5–30 nM cyclophilin was made up to 2520 μl with buffer A in a 3 ml glass cuvette. The cuvette then was preincubated for 30 min on ice. Immediately before the assay, 300 μl of chymotrypsin solution (50 mg/ml in 10 mM HCl) was added, followed by 90 μl of a 3.7 mM stock solution of Suc-Ala-Ala-Pro-PNA in LiCl (470 mM)/TFE. The reaction progress was monitored by the absorbance change at 400 nm that accompanies the hydrolysis of the amide bond and the release of 4-nitroaniline product.

The PPIase activity of some of the compounds of the present invention are shown in table 2.

TABLE 2

| Ligand | Structure | $K_d$ determined by fluorescence assay* | $K_d$ determined by PPIase assay | Resolution of hCypA-Ligand Complex |
|---|---|---|---|---|
| EM 3/11/1 | 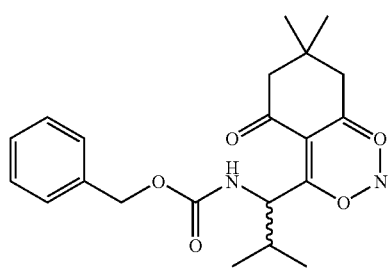 | >25 mM | ND | ND |
| EM 2/40 | 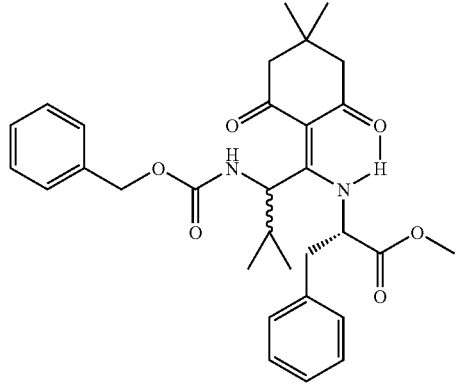 | >25 mM | ND | ND |
| EM 2/34 | 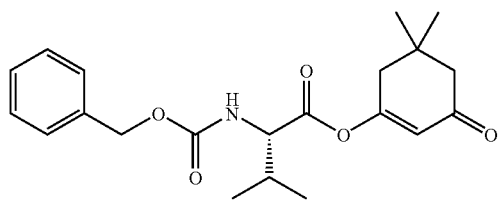 | 1 μM | 23 μM | 1.85 Å<br>R: 18.7%<br>Rfree: 23.3% |
| EM 3/26/1/2 | 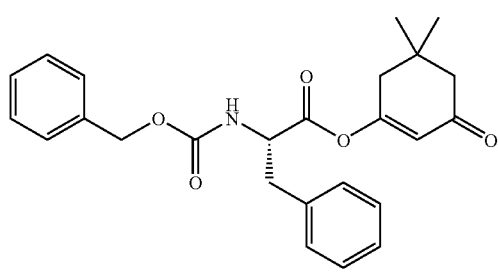 | >25 mM | ND | ND |

TABLE 2-continued

| Ligand | Structure | $K_d$ determined by fluorescence assay* | $K_d$ determined by PPIase assay | Resolution of hCypA-Ligand Complex |
| --- | --- | --- | --- | --- |
| EM 3/26/2/5 | 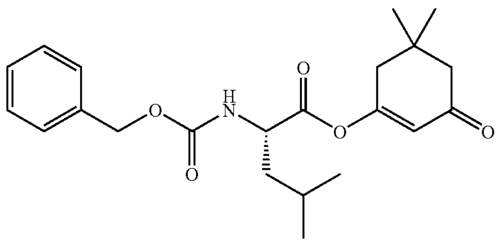 | <25 mM >1 μM | ND | ND |
| EM 3/29/1/1 | 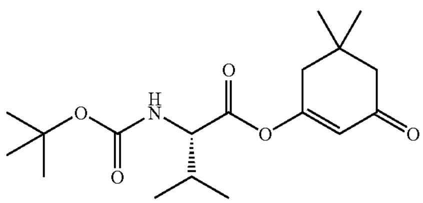 | <25 mM >1 μM | ND | ND |
| EM 3/22/1 | 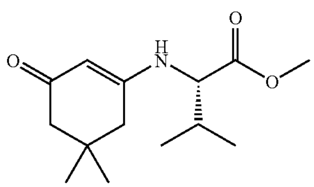 | >25 mM | ND | ND |
| EM 3/27 | 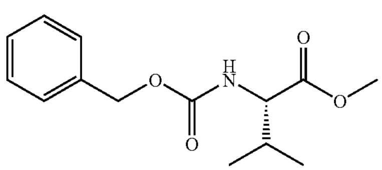 | <25 mM >1 μM | ND | ND |
| EM 4/10/1 | 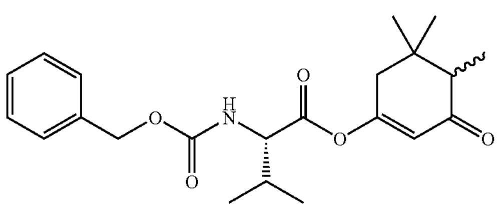 | ND | 20 μM | 2.30 Å R: 18.1% Rfree: 33.1% |
| EM 4/35/1/1 | 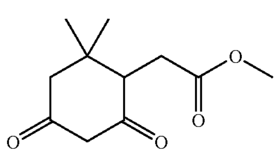 | 45 μM | ND | 1.90 Å R: 20.4% Rfree: 26.0% |
| EM 4/18/1 | 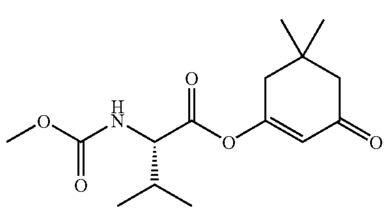 | 70 μM | ND | 1.8 Å R: 20.7% Rfree: 26.8% |

TABLE 2-continued

| Ligand | Structure | $K_d$ determined by fluorescence assay* | $K_d$ determined by PPIase assay | Resolution of hCypA-Ligand Complex |
|---|---|---|---|---|
| EM 5/12/3 | 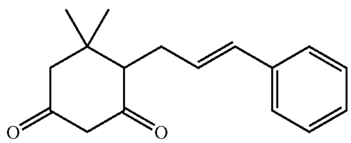 | 85 μM | ND | 2.03 Å<br>R: 18.8%<br>Rfree: 24.9% |
| EM 3/48/2/1 | 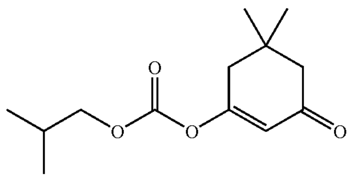 | 130 μM | ND | 2.70 Å<br>R: 21.4%<br>Rfree: 28.4% |
| EM 4/21/1 | 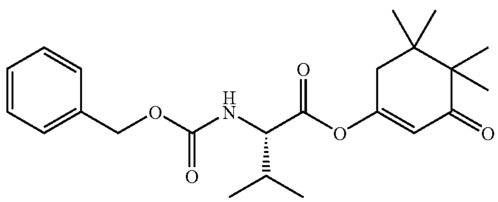 | 68 μM | ND | 2.1 Å<br>R: 20.9%<br>Rfree: 28.6% |
| EM 4/33/1 | 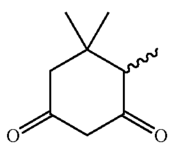 | ND | 134 μM | 2.10 Å<br>R: 20.1%<br>Rfree: 26.8% |

*Determined by fluorescence assay

Fluorescence Assay: Interaction with Cyclophilin D

Further fluorescence titration studies were undertaken to investigate the interaction of selected compounds of the invention with cyclophilin D. The assay was carried out in accordance with the method described in Maurice R. Eftink and Camillo A. Ghiron, [Fluorescence Quenching Studies with Proteins, Analytical Biochemistry 114, 199–227 (1981)]. The results are shown below in Table 3, together with additional data showing the rotamase activity, determined in accordance with the method of Kofron et al (ibid).

TABLE 3

| | | Fluorescence Titration Cyp-D Wild-type | Rotamase activity % Control | | |
|---|---|---|---|---|---|
| Compound | | $K_D$ (μM) | 50 μM | 100 μM | 200 μM |
| Cyclosporin A[a] | | 0.07 | $IC_{50}$ = 0.03 μM | | |
| EM 3/11/1 | | 203 | 109 | 102.5 | 61 |

TABLE 3-continued

| Compound | Fluorescence Titration Cyp-D Wild-type K$_D$ (μM) | Rotamase activity % Control | | |
|---|---|---|---|---|
| | | 50 μM | 100 μM | 200 μM |
| Cyclosporin A[a] | 0.07 | IC$_{50}$ = 0.03 μM | | |
| EM 2/40 | 110 | 96 | 100 | 59 |
| EM 2/34 | 347 | 81 | 80 | 33 |
| EM 3/26/1/2[b] | 154 | 83 | 72.5 | 33 |
| EM 3/26/2/5 | 116 | 79 | 78 | 52 |

TABLE 3-continued

| Compound | K$_D$ (μM) Fluorescence Titration Cyp-D Wild-type | Rotamase activity % Control | | |
|---|---|---|---|---|
| | | 50 μM | 100 μM | 200 μM |
| Cyclosporin A[a] | 0.07 | IC$_{50}$ = 0.03 μM | | |
| EM 3/29/1/1 | 362 | 107 | 77.5 | 50 |
| EM 3/22/1 | 103 | 110 | 102 | 63 |
| EM 3/27[c] | — | 111 | 96 | 60 |
| EM 4/10/1[d] | 815 | 78 | 84.5 | 60 |
| EM 4/12/2 | 107 | 104 | 106.5 | 98 |
| EM 5/11 | 170 | 84 | 99 | 71 |

[a] reference compound: active control
[b] rotamase activity: inhibition of spontaneous isomerisation
[c] no fluorescence change
[d] precipitation at concentration of >100 μM

What is claimed is:

1. A compound of formula I

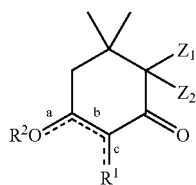

wherein
a and c are single bonds, b is a double bond, and $R^1$ is H, $R^2$ is

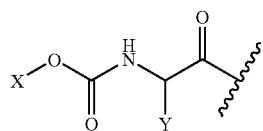

wherein
X is straight or branched chain $C_{1-6}$ alkyl, $-(CH_2)_n Ar$, $C_{1-6}$ cycloalkyl, or $-(CH_2)_n R''$, where R'' is a cyclic hydrocarbyl group;
Y is a natural or unnatural amino acid side chain; and
$Z_1$ and $Z_2$ are each independently H, straight or branched chain $C_{1-6}$ alkyl, straight or branched chain $C_{1-6}$ alkenyl, $-(CH_2)_n Ar$, $-(CH_2)_n-CO_2 R'$, $-(CH_2)_p-CH=CH-(CH_2)_q Ar$ where p and q are each independently 0 to 5, R' is $C_{1-6}$ alkyl;
and each n may be the same or different and is from 1 to 5.

2. The compound according to claim 1, wherein X is selected from methyl, t-butyl, 2-methylpropyl, ethyl, benzyl and

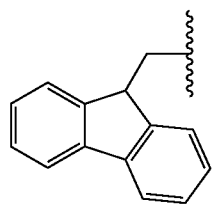

3. The compound according to claim 1, wherein Y is selected from methyl, benzyl, iso-propyl and 2-methylpropyl.

4. The compound according to claim 1, wherein $Z_1$ and $Z_2$ are each independently selected from H, methyl, benzyl, allyl, $-CH_2CO_2Me$ and $-CH_2-CH=CH-Ph$.

5. The compound according to claim 1, wherein said compound is a racemate.

6. The compound according to claim 1, wherein the stereochemistry of the Y substituent is such that the chiral centre to which it is attached is in the (S)-form.

7. The compound according to claim 1, wherein said compound is of formula III

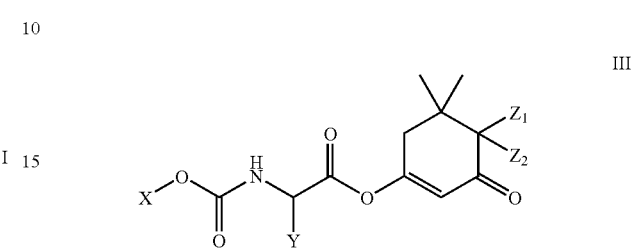

8. The compound according to claim 7, wherein
$Z_1$ and $Z_2$ are each independently selected from H or a straight or branched $C_{1-6}$ alkyl group;
Y is isopropyl, 2-methylpropyl or $CH_2Ph$;
X is $CH_2Ph$ or a straight or branched $C_{1-6}$ alkyl group.

9. The compound according to claim 7, wherein X is $^tBu$ or $CH_2Ph$.

10. The compound according to claim 7, wherein said compound is selected from the following:

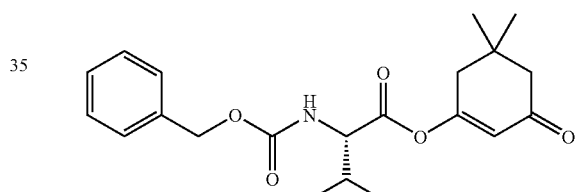

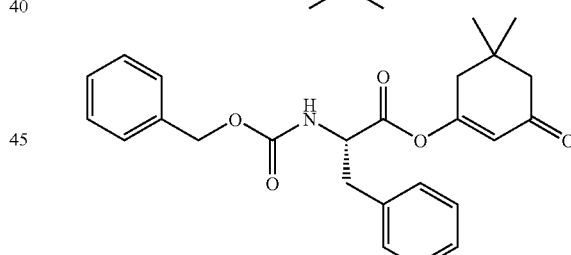

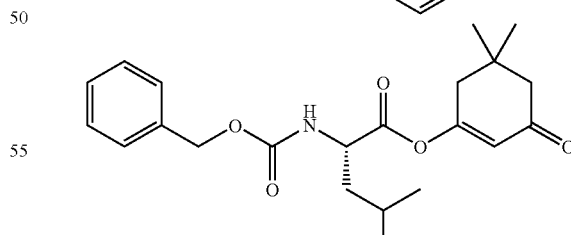

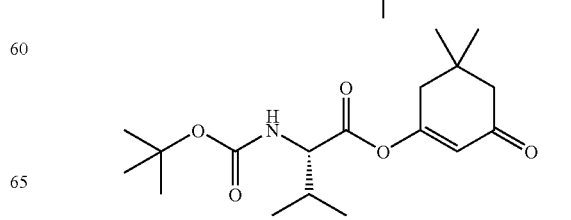

-continued

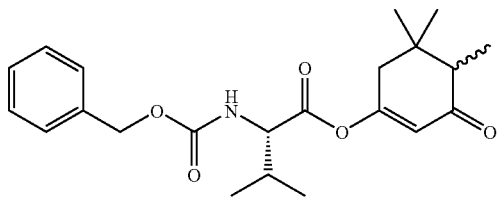

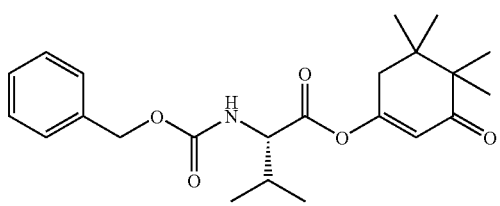

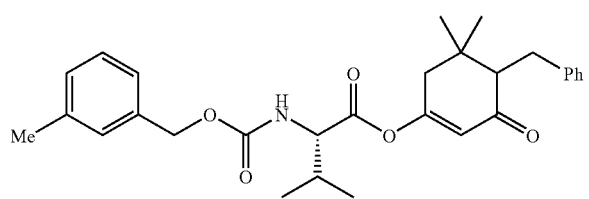

11. A complex comprising cyclophilin and a compound of claim 1.

12. The complex according to claim 11, wherein the cyclophilin is cyclophilin A, cyclophilin D or cyclophilin 40.

13. A pharmaceutical composition comprising a compound according to claim 1, together with a pharmaceutically acceptable diluent, excipient or carrier.

14. A method of detecting spectrophotometrically the binding of a ligand to the PPIase binding site of cyclophilin, said method comprising the steps of:
(i) contacting a ligand with cyclophilin in the presence of a known substrate of cyclophilin; and
(ii) detecting spectrophotometrically any change in the activity in the PPIase activity of cyclophilin on said known substrate; and wherein said ligand is a compound according to claim 1.

15. A method of screening for a ligand capable of binding to a ligand binding domain of a cyclophilin, wherein said ligand binding domain comprises one or more of Phe 113, Arg 55, Gln 111 and Asn 102, the method comprising contacting the ligand binding domain with a test compound and determining spectrophotometrically if said test compound binds to said ligand binding domain, wherein said test compound is of the formula I

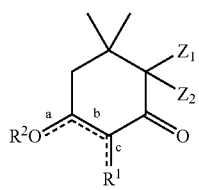

wherein
a and c are single bonds, b is a double bond, and $R^1$ is H, $R^2$ is

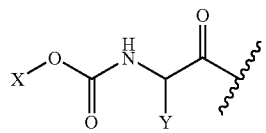

wherein
X is straight or branched chain $C_{1-6}$ alkyl, $-(CH_2)_n Ar$, $C_{1-6}$ cycloalkyl, or $-(CH_2)_n R''$, where R" is a cyclic hydrocarbyl group;
Y is a natural or unnatural amino acid side chain; and
$Z_1$ and $Z_2$ are each independently H, straight or branched chain $C_{1-6}$ alkyl, straight or branched chain $C_{1-6}$ alkenyl, $-(CH_2)_n Ar$, $-(CH_2)_n -CO_2 R'$, $-(CH_2)_p-CH=CH-(CH_2)_q Ar$ where p and q are each independently 0 to 5, R' is $C_{1-6}$ alkyl;
and each n may be the same or different and is from 1 to 5.

16. A method of screening for a ligand capable of binding to a ligand binding domain of a cyclophilin, comprising:
(a) incubating a cyclophilin, a candidate compound and a compound defined in any of claim 1,
(b) observing spectrophotometrically any change in the binding dissociation constant (Kd) as compared to the identical incubation lacking the candidate compound and, if the Kd has decreased,
(c) optionally preparing the candidate compound by conventional means.

17. A method of screening for a ligand capable of binding to a ligand binding domain of a cyclophilin, comprising:
(a) incubating a cyclophilin with a candidate compound,
(b) generating a crystal of said cyclophilin and candidate compound and
(c) observing using X-rat structure determination any interaction between the candidate compound and any of amino acids of the cyclophilin corresponding to Phe 113, Arg 55, Gln 111 and Asn 102 of cyclophilin A, wherein said candidate compound is of the formula I

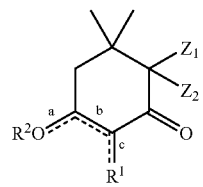

wherein
a and c are single bonds, b is a double bond, and $R^1$ is H, $R^2$ is

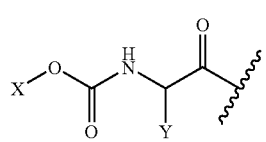

wherein
- X is straight or branched chain $C_{1-6}$ alkyl, —$(CH_2)_n$Ar, $C_{1-6}$ cycloalkyl, or —$(CH_2)_n$R", where R" is a cyclic hydrocarbyl group;
- Y is a natural or unnatural amino acid side chain; and
- $Z_1$ and $Z_2$ are each independently H, straight or branched chain $C_{1-6}$ alkyl, straight or branched chain $C_{1-6}$ alkenyl, —$(CH_2)_n$Ar, —$(CH_2)_n$—$CO_2$R', —$(CH_2)_p$—CH=CH—$(CH_2)_q$Ar where p and q are each independently 0 to 5, R' is $C_{1-6}$ alkyl;
- and each n may be the same or different and is from 1 to 5.

18. A method of screening for a ligand capable of binding to a ligand binding domain of a cyclophilin, wherein said ligand binding domain comprises one or more of Phe 113, Arg 55, Gln 111 and Asn 102, the method comprising contacting the ligand binding domain with a test compound and determining spectrophotometrically if said test compound binds to said ligand binding domain, where said cyclophilin is cyclophilin A, cyclophilin D or cyclophilin 40, and wherein said test compound is of the formula I

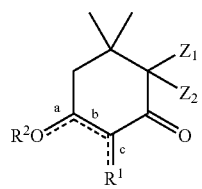

I wherein
- a and c are single bonds, b is a double bond, and $R^1$ is H, $R^2$ is

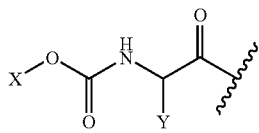

wherein
- X is straight or branched chain $C_{1-6}$ alkyl, —$(CH_2)_n$Ar, $C_{1-6}$ cycloalkyl, or —$(CH_2)_n$R", where R" is a cyclic hydrocarbyl group;
- Y is a natural or unnatural amino acid side chain; and
- $Z_1$ and $Z_2$ are each independently H, straight or branched chain $C_{1-6}$ alkyl, straight or branched chain $C_{1-6}$ alkenyl, —$(CH_2)_n$Ar, —$(CH_2)_n$—$CO_2$R', —$(CH_2)_p$—CH=CH—$(CH_2)_q$Ar where p and q are each independently 0 to 5, R' is $C_{1-6}$ alkyl;
- and each n may be the same or different and is from 1 to 5.

19. A process for preparing a compound of formula III,

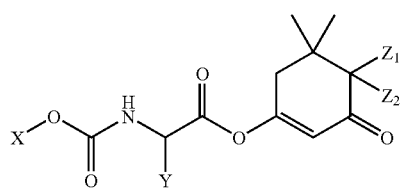

III said process comprising the steps of
(i) reacting a compound of formula V with a compound of formula VI to form a compound of formula VII;

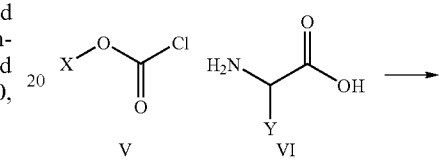

V        VI

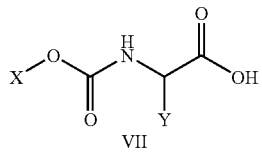

VII (ii) converting said compound of formula VII to a compound of formula VIII by treating said compound of formula VII with $(CFN)_3$/pyridine;

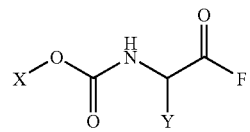

VIII (iii) reacting said compound of formula VIII with a compound of formula IV in the presence of N,N'-diisopropylethylamine

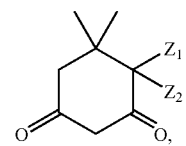

IV such that a compound of formula III is prepaid.

* * * * *